United States Patent
Lee et al.

(10) Patent No.: US 9,457,176 B2
(45) Date of Patent: Oct. 4, 2016

(54) IMPLANTABLE DRUG DELIVERY DEVICE WITH BLADDER RETENTION FEATURE

(75) Inventors: Heejin Lee, Arlington, MA (US); Hong Linh Ho Duc, Watertown, MA (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 13/267,469

(22) Filed: Oct. 6, 2011

(65) Prior Publication Data

US 2012/0089121 A1 Apr. 12, 2012

Related U.S. Application Data

(60) Provisional application No. 61/390,495, filed on Oct. 6, 2010.

(51) Int. Cl.
*A61M 31/00* (2006.01)
*A61K 9/00* (2006.01)

(52) U.S. Cl.
CPC .......... *A61M 31/002* (2013.01); *A61K 9/0034* (2013.01); *A61K 9/0065* (2013.01); *A61M 2210/1085* (2013.01)

(58) Field of Classification Search
CPC ................. A61M 31/002; A61M 2210/1085; A61M 31/00; A61K 9/0034; A61K 9/0065
USPC ........................ 604/57, 285, 287, 288, 517
See application file for complete search history.

(56) References Cited

U.S. PATENT DOCUMENTS

| | | | |
|---|---|---|---|
| 3,786,813 A | 1/1974 | Michaels | |
| 3,788,322 A * | 1/1974 | Michaels | 604/890.1 |
| 4,055,178 A * | 10/1977 | Harrigan | 604/890.1 |
| 4,871,542 A | 10/1989 | Vilhardt | |
| 4,940,465 A | 7/1990 | Theeuwes et al. | |
| 6,171,298 B1 | 1/2001 | Matsuura et al. | |
| 6,183,461 B1 | 2/2001 | Matsuura et al. | |
| 7,074,178 B2 | 7/2006 | Connors et al. | |
| 7,862,552 B2 | 1/2011 | McIntyre et al. | |
| 2004/0037318 A1 | 2/2004 | Salin et al. | |
| 2004/0260272 A1 | 12/2004 | Friedman et al. | |
| 2007/0202151 A1 | 8/2007 | Lee et al. | |
| 2009/0149833 A1 | 6/2009 | Cima et al. | |
| 2010/0003297 A1 | 1/2010 | Tobias et al. | |
| 2010/0330149 A1 | 12/2010 | Daniel et al. | |
| 2010/0331770 A1 | 12/2010 | Lee et al. | |
| 2011/0060309 A1 | 3/2011 | Lee et al. | |
| 2011/0152839 A1 | 6/2011 | Cima et al. | |

FOREIGN PATENT DOCUMENTS

| | | | |
|---|---|---|---|
| WO | 2012018923 A1 | 2/2012 | |
| WO | 2012019155 A1 | 2/2012 | |

* cited by examiner

*Primary Examiner* — Emily Schmidt
(74) *Attorney, Agent, or Firm* — Sutherland Asbill & Brennan LLP

(57) ABSTRACT

Implantable devices and methods for controlled drug delivery are provided. The device includes a device structure deformable between a retention shape and a low profile shape for deployment in the bladder of a patient and has a drug reservoir lumen in which a drug formulation is housed. The device also includes a buoyancy retention portion, which includes a volume of entrapped air or a gas-generating or effervescent powder which will generate a volume of entrapped air following contact with urine in the bladder. The buoyancy retention portion may include a water permeable and/or biodegradable wall, which can release the entrapped air following drug release, to cause the device to sink into the bladder neck to facilitate device expulsion without the need for a device retrieval medical procedure.

33 Claims, 6 Drawing Sheets

IMPLANTABLE DRUG DELIVERY DEVICE WITH BLADDER RETENTION FEATURE

CROSS-REFERENCE TO RELATED APPLICATIONS

This application claims priority to U.S. Provisional Patent Application No. 61/390,495, filed Oct. 6, 2010, which is incorporated herein by reference.

BACKGROUND

U.S. Patent Application Publications No. 2007/0202151 and No. 2009/0149833 describe embodiments of a drug delivery device for minimally invasive deployment and retention in a patient, for example in the bladder. The device resists excretion, such as in response to the forces associated with urination. For example, the device may include a retention frame, which may be configured into a relatively low profile for deployment into the body and may assume a relatively expanded profile once implanted to facilitate retention. The device may provide controlled release of drug over an extended period in a predefined manner.

It would be desirable to provide additional options for retaining such a device in the body, for releasing drug from such a device into the body, and for removal of the device from the body subsequent to drug release. In some cases, it would be desirable to retain the device in the bladder without the need for a retention frame, for example where it is desired that the entire device be degradable/resorbable in vivo.

SUMMARY

Implantable medical devices and methods for controlled drug delivery are provided. In a preferred embodiment, the device includes a device structure which comprises a device body having at least one drug reservoir lumen, the device structure being deformable between a retention shape and a low profile shape for deployment in the bladder of a patient; a drug formulation positioned in the at least one drug reservoir lumen, the drug formulation comprising at least one drug; and at least one buoyancy retention portion, which comprises a volume of entrapped air or a gas-generating or effervescent powder which will generate a volume of entrapped air following contact with urine in the bladder. The buoyancy retention portion may include a water permeable and/or biodegradable wall, which at least in part defines the space containing the volume of the entrapped air. This can enable the release of the entrapped air following drug release to cause the device to sink into the bladder neck so that the device can be exposed to amplified hydrodynamic forces during urination, facilitating device expulsion without the need for a medical procedure for device retrieval.

BRIEF DESCRIPTION OF THE DRAWINGS

FIG. 8 illustrates an embodiment of a drug reservoir portion, wherein

DETAILED DESCRIPTION

Implantable devices are provided that can be deployed in the bladder of patient, such as for release of at least one drug over an extended period. The device advantageously includes a buoyancy feature to facilitate retention of the device in the bladder despite expected forces in the bladder, such as the hydrodynamic forces associated with urination or contraction of the detrusor muscle. Thus, expulsion from the bladder advantageously is impeded or prevented so that the device can deliver a drug into the bladder over an extended time period.

The devices and methods disclosed herein build upon those described in U.S. application Ser. No. 12/333,182, filed Dec. 11, 2008; U.S. application Ser. No. 12/825,215, filed Jun. 28, 2010; and U.S. application Ser. No. 12/972,364, filed Dec. 17, 2010, which are incorporated by reference herein. The devices and methods disclosed herein may be used in humans, whether male or female, adult or child, or in other mammals, such as for veterinary or livestock applications. In one embodiment, the drug delivery device may deliver lidocaine or another anesthetic agent locally to the bladder over an extended period for the treatment of a condition such as IC/PBS, neurogenic bladder, or pain such as post-operative pain.

I. The Implantable Drug Delivery Device

Generally, the implantable drug delivery devices include a drug formulation and a device structure. For purposes of this disclosure, the term "the device structure" generally refers to portions of the device other than the drug formulation.

The device structure includes a drug reservoir portion, a buoyancy retention portion, and optionally a retention frame portion. The drug reservoir portion includes a drug reservoir lumen into which the drug formulation is positioned. The retention frame portion, in some embodiments, includes a retention frame and a retention frame lumen, the retention frame being positioned at least partially within the retention frame lumen. In other embodiments, the retention frame portion includes a retention frame only. The device structure may include a device body that defines the drug reservoir lumen and the retention frame lumen. In other embodiments, the device structure includes a drug reservoir portion, but no retention frame portion. In such embodiments, the device may rely on one or more buoyancy elements, such as retention air elements, to provide the needed bladder retention functionality. Alternatively or in addition, the drug reservoir portion may be made from a material capable of imparting a retention shape to the device.

Figure 1:
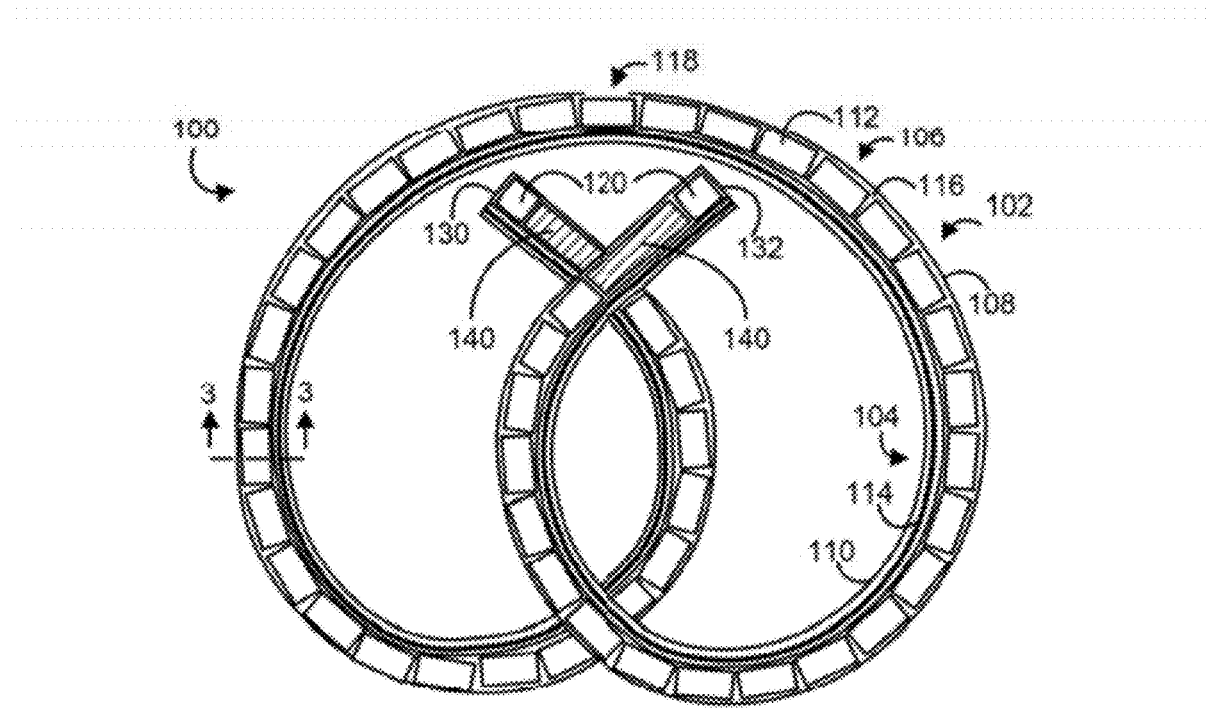
FIG. 1 is a plan view of an embodiment of a drug delivery device having a retention air feature.

An embodiment of a drug delivery device 100 is illustrated in FIG. 1. The device 100 includes a drug reservoir portion 102, a retention frame portion 104, and retention air elements 140. In FIG. 1, the device 100 is shown in a relatively expanded shape suited for retention in the body, especially the bladder, and in FIG. 2 the device 100 is shown in a relatively lower-profile shape for deployment through the channel 202 of a deployment instrument 200, such as a cystoscope or catheter. Following deployment into the body, the device 100 may assume the relatively expanded shape to retain the drug delivery device in the body cavity or lumen, such as the bladder.

For the purposes of this disclosure, terms such as "relatively expanded shape," "relatively higher-profile shape," or "retention shape" generally denote any shape suited for retaining the device in the intended implantation location, including but not limited to the pretzel shape shown in FIG. 1 that is suited for retaining the device in the bladder. Similarly, terms such as "relatively lower-profile shape," "low-profile shape," or "deployment shape" generally denote any shape suited for deploying the drug delivery device into the body, including the linear or elongated shape shown in FIG. 2 that is suited for deploying the device through the working channel of a catheter, cystoscope, or other deployment instrument positioned in a lumen of the body, such as the urethra. In embodiments, the drug delivery device may naturally assume the relatively expanded shape and may be deformed, either manually or with the aid of an external apparatus, into the relatively lower-profile shape for insertion into the body. Once deployed, the device may spontaneously or naturally return to the initial, relatively expanded shape for retention in the body.

In the illustrated embodiment of FIG. 1, the drug reservoir and retention frame portions 102, 104 of the drug delivery device 100 are longitudinally aligned and are coupled to each other along their length, although other configurations are possible. For example, the drug reservoir portion 102 may be attached to the retention frame portion 104 at discrete points but otherwise may be separate or spaced apart from the retention frame portion 104.

In particular, the drug delivery device 100 includes an elastic or flexible device body 106 that defines a drug reservoir lumen 108 and a retention frame lumen 110. The drug reservoir lumen 108 is designed to house a drug formulation, such as a number of solid drug tablets 112, to form the drug reservoir portion 102. The retention frame lumen 110 is designed to house a retention frame 114 to form the retention frame portion 104. The illustrated lumens 108, 110 are discrete from each other, although other configurations are possible.

Figure 3:
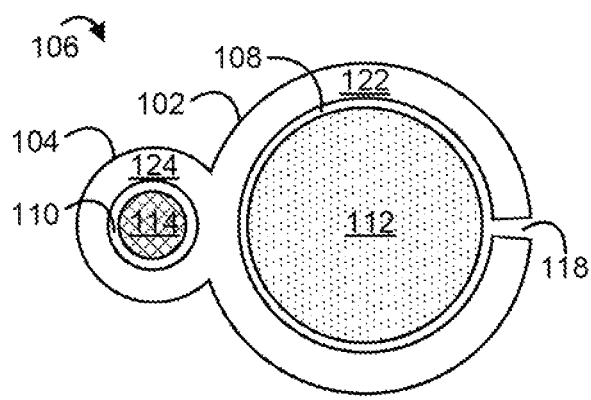
FIG. 3 is a cross-sectional view of the drug delivery device shown in FIG. 1, taken along line 3-3 in FIG. 1.

As shown in the cross-sectional view of FIG. 3, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment may be used, as shown, for example, in FIG. 4.

An aperture 118 may be formed through the wall 122 that defines the drug reservoir lumen 108. The aperture 118 may provide a passageway for releasing drug from the drug reservoir lumen 108 as further described below. However, the aperture 118 may be omitted in some embodiments.

As shown in FIG. 1, the drug reservoir lumen 108 is loaded with a number of drug units 112 in a serial arrangement. For example, between about 10 and about 100 drug units 112 may be loaded, such as between about 30 and about 70 drug units 112, or more particularly between about 50 and 60 drug units 112. However, any number of drug units may be used. The drug reservoir lumen 108 includes an entry 130 and an exit 132, which are shown as relatively circular openings at opposite ends of the drug reservoir lumen 108. The entry 130 provides ingress for the drug units 112 to be placed into the drug reservoir lumen 108 during device loading and assembly. Once the drug units 112 are loaded, at least two end plugs 120 block the entry 130 and exit 132. The end plugs 120 may be cylindrical plugs inserted into the entry 130 and the exit 132, each having a slightly larger outer diameter than an inner diameter of the drug reservoir lumen 108 so that the plugs substantially enclose the entry 130 and exit 132 and are snugly retained in position. In some cases, a number of end plugs 120 can be positioned in the entry 130 or the exit 132. The end plugs 120 may be silicone plugs. The end plugs 120 also may be omitted, in which case the entry 130 and exit 132 may be closed with a material, such as adhesive, that is placed in the drug reservoir lumen 108 in workable form and cures therein.

In some embodiments, the drug tablets 112 may not fill the entire drug reservoir lumen 108. In such embodiments, a filling material may be used to fill the remainder of the drug reservoir lumen 108. For example, the drug tablets 112 may be loaded in a central portion of the drug reservoir lumen 108 and the filling material may be loaded in the remaining end portions of the drug reservoir lumen 108. The filling material may be inserted into the end portions of the drug reservoir lumen 108 after the lumen is filled with the drug tablets 112. The filling material may be a polymeric material. The polymeric material may be placed in the drug reservoir lumen 108 in workable form and may cure therein. Suitable polymeric materials may cure at room temperature or in response to an external stimulus, such as heat. In some cases, the filling material may enclose the entry 130 and exit 132, in which case the end plugs 120 may or may not be provided. The filling material also may be a number of end plugs 120 inserted into the end portions of the drug reservoir lumen 108.

Once the drug units 112 are loaded, interstices 116 or breaks may be formed between adjacent drug units 112. The drug delivery device 100 may be relatively flexible or deformable despite being loaded with a solid drug, as each drug unit 112 may be permitted to move with reference to adjacent drug units 112. Along the length of the drug reservoir lumen 108, the drug units 112 may have the same composition or may vary in composition, and in some cases drug units 112 of different compositions may be in distinct reservoirs that are segregated, either axially or radially, along the length of the drug reservoir lumen 108.

The retention frame lumen 110 is loaded with the retention frame 114, which may be an elastic wire. The retention frame 110 may be configured to spontaneously return to a retention shape, such as the illustrated "pretzel" shape or another coiled shape. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return to the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once implanted, limiting or preventing accidental expulsion.

The material used to form the device body 106 may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases. The flexible material also allows the device body 106 to flex outward or circumferentially expand in response to a flow of pressurized gas through the drug reservoir lumen 108 during drug loading, as described below. The material used to form the device body 106 also may be water permeable or porous so that solubilizing fluid can enter the drug reservoir portion 102 to solubilize the drug units 112 once the device is implanted. For example, silicone or another biocompatible elastomeric material may be used.

Figure 4:
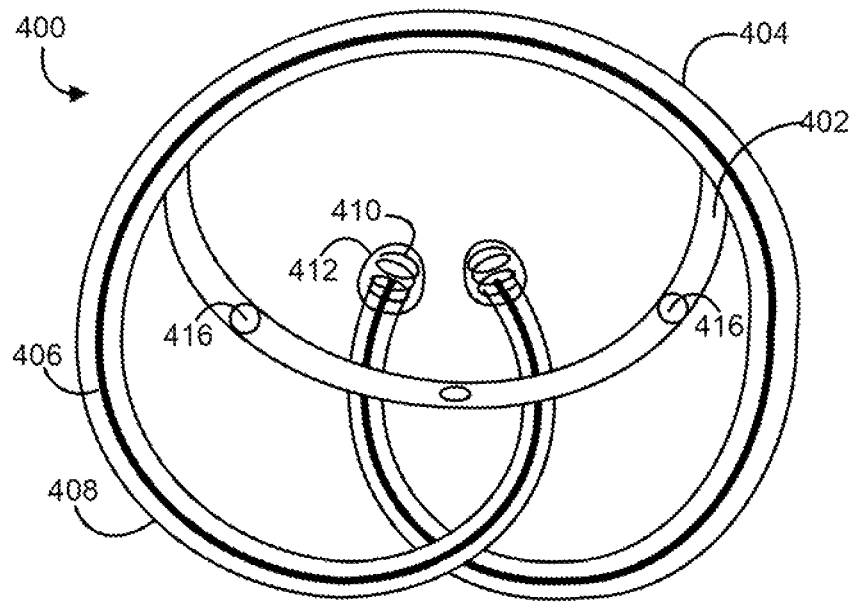
FIG. 4 is a plan view of an embodiment of a drug delivery device.

Another embodiment of a drug delivery device 400 is shown in FIG. 4. The device 400 includes a drug reservoir lumen 402 and a retention frame lumen 404. The drug reservoir lumen 402 is attached to discrete points on the retention frame lumen 404 but is otherwise separate or spaced apart from the retention frame lumen 404. In the drug reservoir lumen 402 are ball-shaped sealing structures 416 designed for retaining the drug (not shown) in the drug reservoir lumen 402. The retention frame 406 is disposed within the retention frame lumen 404. The retention frame lumen 404 is also coated with a polymer coating 408, which may be designed to control the onset of the elimination period. In FIG. 4, the device 400 is shown in a relatively expanded shape suited for retention in the body, and in FIG. 5 the device 400 is shown in a relatively lower-profile shape for deployment through the channel 500 of a deployment instrument, such as a cystoscope or other catheter. Following deployment into the body, the device 400 may assume the relatively expanded shape to retain the drug delivery device in the bladder. Although not shown in FIG. 4, the drug delivery device 400 may be loaded with drug units similar to those described with reference to FIGS. 1-3, and interstices or breaks may be formed between the drug units so that the device 400 is flexible.

Buoyancy Retention Portion

The drug delivery device includes a buoyancy retention portion. The buoyancy of the device may facilitate retaining the device in the bladder during urination. The device may remain above the bladder neck, which experiences increased hydrodynamic forces during urination due to its reduced cross-section. The device may be designed to float in the bladder when filled with urine so that device resists becoming entrained into the urethra during voiding. In some embodiments of the device, the buoyancy feature may be selectively deactivated to enable device retrieval or removal by voiding. In addition, buoyancy may enhance the deployed device's tolerability to the patient.

In preferred embodiments, the buoyancy retention portion includes a volume of retention air. The air decreases the density of the device, causing the device to rise or float within the bladder. As used herein, the term "float" indicates that the device either remains near the dome of the bladder or that the device is elevated or raised within the bladder due to its decreased density. The increased elevation of the device in the bladder allows the device to experience decreased hydrodynamic forces during urination, resisting excretion.

Figure 13:
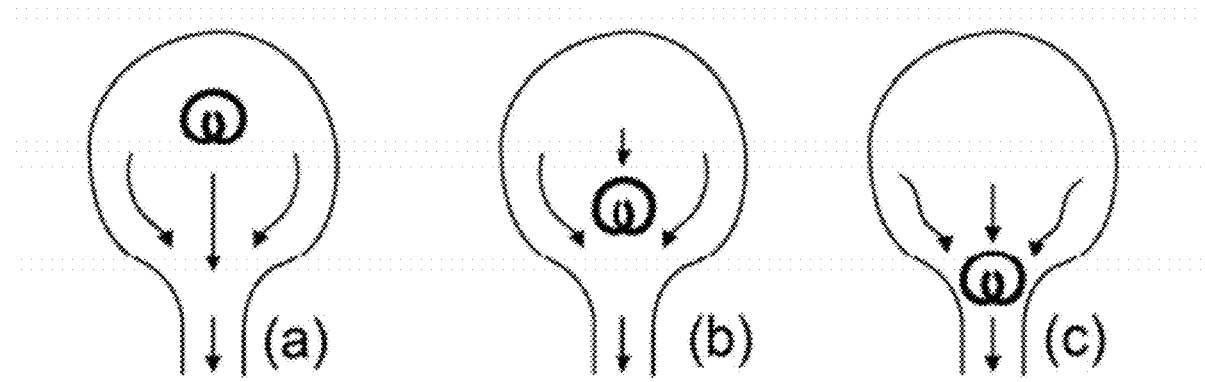
FIG. 13 illustrates schematic cross-sectional views of the bladder, demonstrating potential locations of a drug delivery device in the bladder in response to hydrodynamic forces associated with urination.

In particular, the bladder exhibits a reduced cross-sectional area at the bladder neck, where urine exits the bladder into the urethra during urination. The reduced cross-section results in an increased urine flow rate at the bladder neck, which increases the hydrodynamic forces on the device. In particular, the hydrodynamic forces are proportional to the square of the urine flow rate. Thus, the hydrodynamic forces are relatively higher in the vicinity of the bladder neck during urination than in other bladder locations. Examples are shown in FIG. 13, which illustrates schematic cross-sectional views of the bladder and demonstrates potential locations of a drug delivery device in the bladder. In particular, FIG. 13(a) illustrates the device floating near the dome of the bladder, FIG. 13(b) illustrates the device floating within the middle of the bladder, and FIG. 13(c) illustrates the device sitting in the bladder neck. If the device sits in the bladder neck right before urination as shown in FIG. 13(c), the device experiences increased hydrodynamic forces, risking expulsion. By elevating the device above the bladder neck as shown in FIG. 13(a) or (b), the device may be less likely to be excreted.

The air may be located in any portion of the device, including within the drug reservoir portion, within a retention frame portion, within a separate retention air portion, or any combination thereof. However, in a preferred embodiment, entrapped gas or other buoyancy means are provided at the end portions of the device body, as it is believed that this may aid retention of the device in the bladder by keeping the ends from becoming entrained in the bladder neck during urination.

The volume of the air may be sufficient to facilitate floatation and may vary depending on, for example, the weight of the device. In some embodiments, the air may be present in the device during implantation. In other embodiments, the air may be introduced into the device following implantation. In still other embodiments, the air may be created within the device following implantation.

The term "air" as used herein refers to any gas that is suitable for use within the body. For example, it may be actual air, carbon dioxide, nitrogen, helium, or another, preferably inert, gas.

As shown in FIG. 1, the drug delivery device 100 includes a pair of retention air elements 140 disposed in the ends of the drug reservoir lumen 108. In other embodiments, 1 or 3 or more retention air elements may be included in the device. In other embodiments, the one or more retention air elements may be located in other portions of the device structure.

The retention air elements 140 may be constructed in a number of ways to entrap air within each element or within the device body. The retention air element may be a hollow capsule or a closed-cell foam, such as a foamed biocompatible polymer. In one embodiment, the hollow capsule may be formed of a biodegradable material. In another embodiment, the retention air element may be formed of a radioopaque material to facilitate imaging of the deployed device. In one embodiment, the hollow capsule is elastic, such as a balloon, and contains air under pressure. In another embodiment, the capsule is rigid. The interior of the rigid hollow capsule may be evacuated.

The retention air element may be a separate component that is loaded into the device structure. In another embodiment, the walls enclosing the air may be integral with the walls defining the drug reservoir lumen and/or the retention frame lumen.

Figure 14:
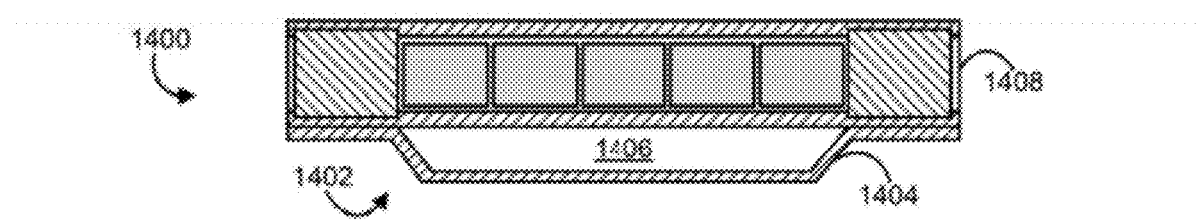
FIG. 14 is a plan cross-sectional view of an embodiment of a device that includes a retention air portion.

FIG. 14 is a plan cross-sectional view of an embodiment of a device 1400 that includes a retention air portion 1402. The retention air portion 1402 includes a wall 1404 that defines an internal lumen and a volume of air 1406 housed within the internal lumen. The wall 1404 may be positioned adjacent to the device 1400, spaced apart from the device to form the lumen, and ends of the wall may be sealed to the device 1400 using, for example, a medical-grade silicone adhesive. Such a configuration may reduce the cross-sectional area of the device 1400 along at least its ends. In other embodiments, other configurations are possible. For example, the retention air portion 1402 may be a tube that is sealed on its ends using, for example, sealing plugs. It is noted that the illustrated device shows the retention air portion 1402 of the device attached to the drug delivery portion 1408 of the device, and the retention frame portion is not shown for simplicity. However, other configurations are possible. Further, only one retention air portion 1402 is shown by way of example, but any number of retention air portions may be provided.

In some embodiments, the wall of the retention air portion may be formed from a water-permeable material, such as in embodiments in which the wall is made from the same materials of construction as the remainder of the device. For example, the device may include a unitary silicone body having multiple discrete lumens for housing drug, a retention frame, and air. The silicone body may have walls that are thin enough about at least the lumen that houses the drug so that water can enter for the purpose of solubilizing the drug. In such embodiments, the body may be made non-water-permeable about the retention air portion so that water cannot enter that portion of the device, causing sinking. For example, a silicone device body may have an increased wall thickness along the retention air portion to decrease its permeability to water. The wall of the retention air portion also may be formed from a material that is not permeable to water, or the wall of the retention air portion may be coated in a material that is not permeable to water, such as a parylene coating. Any combination of these configurations may be employed.

Introducing or creating the air in the device following implantation may facilitate device deployment, as the device may have a relatively smaller cross-sectional area before being loaded with air. In embodiments in which the device has a separate retention air portion, the retention air portion may be collapsed or compressed into a deployment position when unfilled, which reduces the size of the device for deployment through a catheter or other deployment instrument. Once the device is implanted, air may be introduced into or created within the retention air portion, causing it to expand to the filled state for retention.

Figure 15:
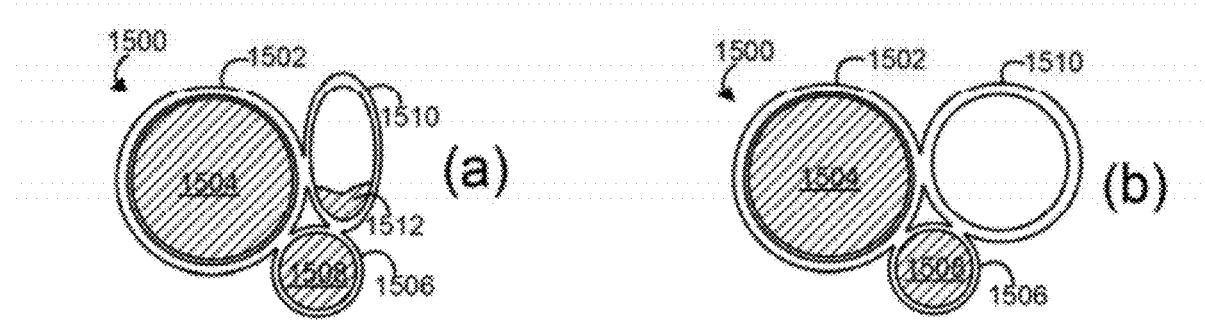
FIG. 15 is a plan cross-sectional view of an embodiment of a drug delivery device that includes a retention air portion, illustrating the retention air portion in an a deployment position and in a retention position.

An example is shown in FIG. 15, which is a side cross-sectional view of an embodiment of a drug delivery device 1500 that includes a drug delivery portion 1502 housing a drug 1504, a retention frame portion 1506 housing a retention frame 1508, and a retention air portion 1510. The retention air portion 1510 is shown in an unfilled state in FIG. 15(a) and in a filled state in FIG. 15(b). In the unfilled state, the retention air portion 1510 may collapse into a deployment position of reduced size for deployment through a catheter or other deployment instrument, as shown in FIG. 15(a). Once the device is implanted, air may be introduced into or created within the retention air portion 1510, causing it to expand to the filled state shown in FIG. 15(b) for retention.

In some embodiments, the air is created in the retention air portion following implantation by a gas-generating or effervescent powder. Before the device is implanted in the body, the gas-generating powder fills only a portion of the retention air portion, so that the retention air portion can be collapsed or otherwise reduced in size for deployment. An example of a gas-generating powder 1512 is shown in the retention air portion 1510 of the device 1500 in FIG. 15. Following implantation, the effervescent powder may generate a gas directly within the retention air portion causing the retention air portion to expand for retention. For example, the gas-generating powder may generate a gas upon contact with urine. The urine may permeate directly through the wall of the retention air portion, which may be water permeable along at least a portion, causing the powder to generate gas. The generated gas increases the pressure inside the retention air portion to a level that is sufficient to prevent further water permeation. The retention air portion may be inflated or ballooned slightly by the generated gas.

The gas-generating or effervescent powder may be composed of a variety of effervescent materials. These materials typically are effervescent couples of an organic acid or its acidic salt, and an alkali metal bicarbonate or carbonate. Examples of the organic acid or its acidic salt include citric acid, malic acid, tartaric acid, adipic acid, fumaric acid, succinic acid, ascorbic acid, maleic acid, alginic acid, sodium dihydrogen phosphate, and disodium hydrogen phosphate. Examples of the alkali metal bicarbonate or carbonate include sodium bicarbonate, potassium bicarbonate, calcium carbonate, sodium carbonate, and potassium carbonate. In other embodiments, the gas-generating or effervescent powder may be organic acid free, as described in U.S. Patent Application Publication No. 2010/0074849 to Rau. In such an embodiment, the powder may comprise, for example, a combination of magnesium chloride and sodium bicarbonate.

The gas-generating or effervescent powder may include other constituents, such as water soluble binders and lubricants known in the art. For example, the binder may be lactose, xylitol, dextrose, sorbitol latose, maltilol, among others, and the lubricant may be sodium benzoate, polyethylene glycol, adipic acid, among others. The gas-generating or effervescent powder may be formulated and provided in a loose or compacted form (e.g., particulate or tablet form) for loading into the drug delivery device.

Figure 16:
FIG. 16 illustrates perspective views of embodiments of drug delivery devices having air retention features.

In some embodiments, the air retention portion may be the only feature that retains the device in the bladder. In other words, the retention frame may be omitted. In such embodiments, the device includes a drug delivery portion associated with an air retention portion. The drug delivery portion houses the drug, and the air retention portion houses a volume of entrapped air. The entrapped air may retain the device at or near the dome of the bladder during implantation. Examples of such devices are shown in FIG. 16. As described above, the air retention portion may be filled with air before the device is implanted, or the air retention portion may include a gas-generating powder that forms a gas upon contact with urine, in which case at least a portion of the wall about the air retention portion may be water permeable. The air retention portion may be made of thin and inflatable material so that it can be inflated or have increased volume by a gas-generating powder, thus imparting increased buoyancy to the device. The illustrated devices 1600 are cylindrically shaped and include an internal wall 1606 that divides the device into two compartments, a drug compartment 1602 housing a drug 1604 and an air compartment 1608 housing air 1610. However, the device can have a variety of other configurations or shapes, such as a bullet-shape, among others. For this cylindrical or bullet shaped device, the overall size of the device is preferred to be larger than the ureteral orifice size, which is about 3-4 mm in diameter, to prevent the floating device from migrating into the ureter.

In some embodiments, the device is designed to release the retention air in vivo at some point following drug release. The release of the air may cause the device to sink into the bladder neck so that the device is exposed to amplified hydrodynamic forces during urination, facilitating device expulsion. The air may be released from the retention air portion in a variety of manners. For example, the wall of the retention air portion may be formed from a material that at least partially degrades or erodes in vivo at a selected time following implantation. Thus, the air may be released from the retention air portion causing the device to sink. As another example, the wall of the retention air portion may become water-permeable at a selected time following implantation. One example is a retention air portion formed from a water-permeable wall, which is coated in non-water-permeable coating that erodes or degrades at some point following implantation. Thus, water may enter the retention air portion at a selected time, causing the device to sink. In such embodiments, the device may be sized and shaped so that the device can be spontaneously and naturally voided upon sinking. For example, the device may have an apparent diameter of 5 mm or less so that the device can pass through the urethra. To achieve the desired drug load, multiple discrete devices can be deployed into the bladder at the same time in such embodiments. Such configurations facilitate expelling the device from the body without a separate medical procedure. The patient also may be directed to increase their liquid consumption for the purpose of artificially increasing the hydrodynamic forces in the bladder to further ease expulsion.

In some embodiments, the device in the dry and loaded configuration has a density that is less than the density of water, such as a density that is less than 1 g/mL. In addition or instead of a retention air portion, the device body may be composed of lighter or lower density materials to compensate for any higher density drug or other payload in the device, thereby maintaining an overall density that facilitates buoyancy.

Device Dimensions

In one embodiment in which the drug delivery device is designed to be implanted in the bladder, the drug delivery device is designed to be inserted into the bladder through the urethra cystoscopically. Thus, the device may be sized and shaped to fit through a narrow tubular path of a deployment instrument, such as a catheter or cystoscope.

Typically, a cystoscope for an adult human has an outer diameter of about 5 to 7 mm and a working channel having an inner diameter of about 2.4 mm to about 2.6 mm. In other embodiments, a cystoscope has a working channel with a larger inner diameter, such as an inner diameter of 4 mm or more. Thus, the device may be relatively small in size. For example, when the device is elastically deformed to the relatively lower profile shape, the device for an adult patient may have a total outer diameter that is about 3.75 mm or less, such as about 2.6 mm or less. For pediatric patients, the dimensions of the device are anticipated to be smaller. In addition to permitting insertion, the relatively small size of the device may also reduce patient discomfort and trauma to the bladder.

Figure 7:
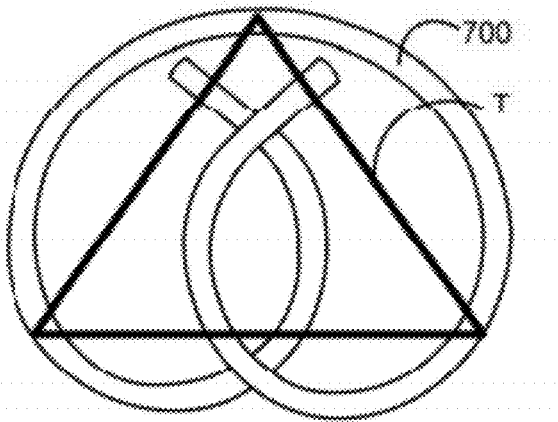
FIG. 7 is an illustration showing the size of an embodiment of a drug delivery device in comparison to an approximation of the bladder trigone region.

The overall configuration of the device preferably is designed to ensure that the device is tolerable to the patient while it is deployed in vivo, as described in U.S. Patent Application Publication No. 2011/0152839 A1 to Cima et al., which is incorporated herein by reference. FIG. 7 shows an example triangle T that approximates the trigone of an adult human male. In a human male, the distance from the bladder neck to one of the ureteral orifices is about 2.75 cm and the distance between the two ureteral orifices is about 3.27 cm. Thus, in FIG. 7, the distance from the top vertex to either of the bottom vertices is about 2.8 cm, while the distance between two bottom vertexes is 3.3 cm. The size of the trigone region may vary depending on the animal. In an adult human female, for example, the distance between the two ureteral orifices is about 2.68 cm and the distance from a neck of the bladder to one of the ureteral orifices is about 2.27 cm. Smaller animals may have smaller trigone regions.

The device geometry may be customized to avoid or minimized undesirable contact forces and pressures linked to urgency sensation. Within the three-dimensional space occupied by the device in the retention shape, the maximum dimension of the device in any direction is less than 10 cm, the approximate diameter of the bladder when filled. In some embodiments, the maximum dimension of the device in any direction may be less than about 9 cm, such as about 8 cm, 7 cm, 6 cm, 5 cm, 4.5 cm, 4 cm, 3.5 cm, 3 cm, 2.5 or smaller. In particular embodiments, the maximum dimension of the device in any direction is less than about 7 cm, such as about 6 cm, 5 cm, 4.5 cm, 4 cm, 3.5 cm, 3 cm, 2.5 cm or smaller. In preferred embodiments, the maximum dimension of the device in any direction is less than about 6 cm or smaller.

More particularly, the three-dimension space occupied by the device 700 is defined by three perpendicular directions. Along one of these directions the device has its maximum dimension, and along the two other directions the device may have smaller dimensions. For example, the smaller dimensions in the two other directions may be less than about 4 cm, such as about 3.5 cm, 3 cm, or less. In a preferred embodiment, the device has a dimension in at least one of these directions that is less than 3 cm.

The overall shape of the device may enable the device to reorient itself within the bladder to reduce its engagement or contact with the bladder wall. For example, the overall exterior shape of the device may be curved, and all or a majority of the exterior or exposed surfaces of the device may be substantially rounded. The device also may be substantially devoid of sharp edges, and its exterior surfaces may be formed from a material that experiences reduced frictional engagement with the bladder wall. Such a configuration may enable the device to reposition itself within the empty bladder so that the device applies lower contact pressures to the bladder wall. In other words, the device may slip or roll against the bladder wall into a position in which the device experiences less compression.

An example of a device that generally satisfies these characteristics is shown in FIGS. 1-5. In particular, the illustrated devices are generally planar in shape even though the device occupies three-dimensional space. Such devices may define a minor axis, about which the device is substantially symmetrical, and a major axis that is substantially perpendicular to the minor axis. The device may have a maximum dimension in the direction of the major axis that does not exceed about 6 cm, and in particular embodiments is less than 5 cm, such as about 4.5 cm, about 4 cm, about 3.5 cm, about 3 cm, or smaller. The device may have a maximum dimension in the direction of the minor axis that does not exceed about 4.5 cm, and in particular embodiments is less than 4 cm, such as about 3.5 cm, about 3 cm, or smaller. The device is curved about substantially its entire exterior perimeter in both a major cross-sectional plane and a minor cross-sectional plane. In other words, the overall exterior shape of the device is curved and the cross-sectional shape of the device is rounded. Thus, the device is substantially devoid of edges, except for edges on the two flat ends, which are completely protected within the interior of the device when the device lies in a plane. These characteristics enable the device to reorient itself into a position of reduced compression when in the empty bladder.

The device also may be small enough in the retention shape to permit intravesical mobility. In particular, the device when deployed may be small enough to move within the bladder, such as to move freely or unimpeded throughout the entire bladder under most conditions of bladder fullness, facilitating patient tolerance of the device. Free movement of the device also facilitates uniform drug delivery throughout the entire bladder, as opposed to a particular bladder location located near the release orifice. However, devices that otherwise move freely within the bladder may be impeded from moving freely when the bladder is empty, and yet the device may still be tolerable if sufficiently compressible as described above.

The implantable drug delivery device can be made to be completely or partially bioerodible or biodegradable so that no explantation, or retrieval, of the device is required following release of the drug formulation. The device structure may include at least one biodegradable portion and at least one non-degradable portion. In other embodiments, the device structure is non-degradable. As used herein, the term "bioerodible" or "biodegradable" means that the device, or part thereof, degrades in vivo by dissolution, enzymatic hydrolysis, erosion, resorption, or a combination thereof. In one embodiment, this degradation occurs at a time that does not interfere with the intended kinetics of release of the drug from the device. For example, substantial erosion of the device may not occur until after the drug formulation is substantially or completely released. In one embodiment, the device is erodible and the release of the drug formulation is controlled at least in part by the degradation or erosion characteristics of the erodible device body. In other embodiments, at least a portion of the device structure is not biodegradable and is excreted from the body substantially intact. Upon degradation of the biodegradable portions of the device structure or other deactivation of the retention shape/feature, the non-biodegradable portion may experience a change in size, shape, or configuration that enables the non-biodegradable portion to be excreted from the body.

In some embodiments, the device is at least partially non-bioerodible. Suitable materials of construction may include medical grade silicone, natural latex, PTFE, ePTFE, PLGA, PGS, stainless steel, nitinol, elgiloy (non ferro magnetic metal alloy), polypropylene, polyethylene, polycarbonate, polyester, nylon, or combinations thereof. Following release of the drug formulation, the device and/or the retention frame may be removed substantially intact or in multiple pieces. In some embodiments, the device is partially bioerodible so that the device, upon partial erosion, breaks into non-erodible pieces small enough to be excreted from the bladder. Useful biocompatible erodible and non-erodible materials of construction are known in the art.

Drug Reservoir Portion

Generally, the drug delivery device includes at least one drug reservoir portion. The drug reservoir portion includes the part of the device body that forms at least one drug reservoir lumen, which houses a drug formulation of at least one drug.

In embodiments, the drug reservoir portion is bounded by a sidewall, and a drug formulation is contained within the resulting drug reservoir lumen. The drug reservoir lumen may comprise an elastic tube. In embodiments, the elastic tube is a polymeric tube. In one embodiment, the drug reservoir lumen of the device includes an elongated tube. An interior of the tube may define one or more drug reservoirs, and a drug formulation may be housed in the drug reservoir(s). In another embodiment, the drug reservoir lumen is in a form other than a tube.

The release rate of the drug from the drug reservoir portion generally is controlled by the design of the combination of the device components, including but not limited to the materials, dimensions, surface area, and apertures of the drug reservoir portion, as well as the particular drug formulation and total mass of drug load, among others.

Figure 2:
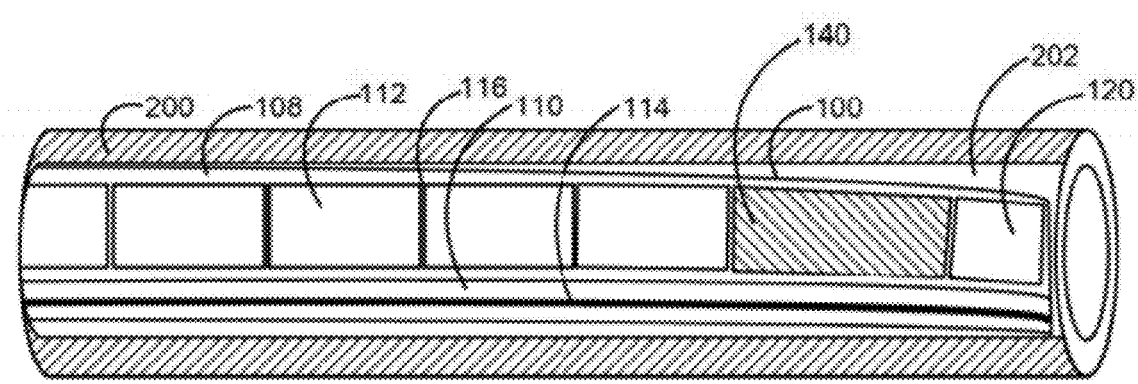
FIG. 2 is a plan view of the drug delivery device shown in FIG. 1, illustrating the drug delivery device inside a deployment instrument.

An example of a drug reservoir portion is shown in FIGS. 1-3. As shown, the drug reservoir portion 102 may include a body formed from an elastomeric tube 122. The tube 122 defines a reservoir 108 that contains a number of drug tablets 112. Ends of the tube 122 may be sealed with sealing structures 120. At least one aperture 118 may be disposed in the tube 122.

Figure 8A:
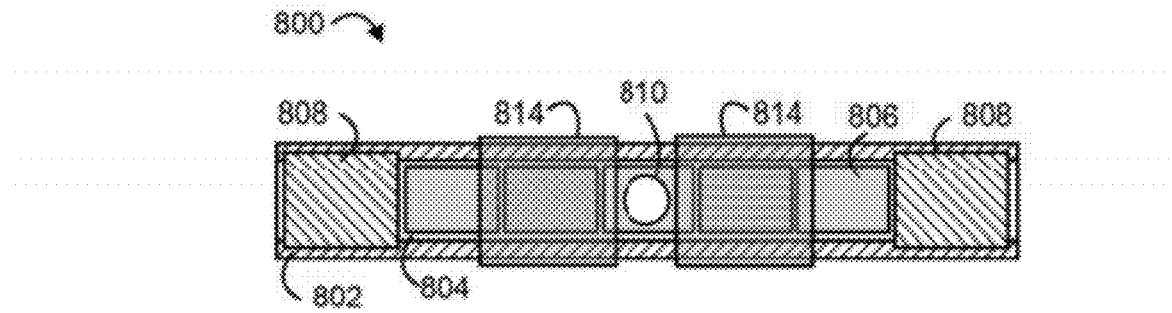
FIG. 8A is a plan view and FIG. 8B is a side cross-sectional view.
Figure 8B:
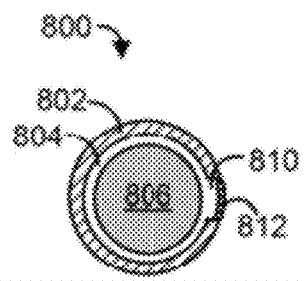

Another example of such a drug reservoir portion is shown in FIGS. 8A and 8B. As shown, the drug reservoir portion 800 generally includes a body formed from an elastomeric tube 802. The tube 802 defines a reservoir 804 that contains a number of drug tablets 806. Ends of the tube 802 may be sealed with sealing structures 808, described below. At least one aperture 810 may be disposed in the tube 802. In cases in which an aperture 810 is provided, the aperture 810 may be closed by a degradable timing membrane 812, which may control the initiation of release of the drug formulation from the reservoir. In some cases, a sheath or coating 814 may be positioned about at least a portion of the tube 802 to control or reduce the release rate, such as by reducing the osmotic surface area of the tube or by reducing diffusion through the tube wall. For simplicity, the sheaths or coatings 814 are not shown in FIG. 8B. Additional examples are shown in FIGS. 1-4.

In one embodiment, the drug reservoir portion operates as an osmotic pump. In such embodiments, the tube may be formed from a water permeable material, such as a silicone, or tube may have a porous structure, or both. Following implantation, water or urine permeates through the wall of the tube, one or more apertures formed through the tube, or one or more passing pores formed through a porous tube. The water enters the reservoir, and is imbibed by the drug formulation. Solubilized drug is dispensed at a controlled rate out of the reservoir through the one or more apertures, driven by osmotic pressure in the reservoir. The delivery rate and overall performance of the osmotic pump is affected by device parameters, such as the surface area of the tube; the permeability to liquid of the material used to form the tube; the shape, size, number and placement of the apertures; and the drug formulation dissolution profile, among other factors. The delivery rate can be predicted from the physicochemical parameters defining the particular drug delivery system, according to well known principles. In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Application Publication No. 2009/0149833.

In an alternative embodiment, the device may operate essentially by diffusion of the drug from the tube through (i) one or more discrete apertures formed in the wall of the tube, or passing pores formed in the wall of a porous tube, or (ii) through the wall of the tube itself, which may be permeable to the drug, or (iii) a combination thereof. In embodiments in which diffusion occurs through the wall, the apertures or passing pores may not be included. In still other embodiments, the device may operate by a combination of osmosis and diffusion.

The drug reservoir portion may be formed from an elastomeric material, which may permit elastically deforming the device for its insertion into a patient, e.g., during its deployment through deployment instrument such as a cystoscope or catheter. For example, the tube may be elastically deformed along with the retention frame for intravesical implantation, as described in further detail below.

In preferred embodiments, the drug reservoir portion is formed from a material that is both elastomeric and water permeable. One material that is both elastomeric and water permeable is silicone, although other biocompatible materials may be used.

The length, diameter, and thickness of the tube may be selected based on the volume of drug formulation to be contained, the desired rate of delivery of the drug from the tube, the intended site of implantation of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

In some embodiments, the device body is non-resorbable. It may be formed of a medical grade silicone tubing, as known in the art. Other examples of suitable non-resorbable materials include synthetic polymers selected from poly (ethers), poly(acrylates), poly(methacrylates), poly(vinyl pyrolidones), poly(vinyl acetates), poly(urethanes), celluloses, cellulose acetates, poly(siloxanes), poly(ethylene), poly (tetrafluoroethylene) and other fluorinated polymers, poly (siloxanes), copolymers thereof, and combinations thereof.

In some embodiments, the device body is bioerodible. In one embodiment of a bioerodible device, the device body is formed of a biodegradable or bioresorbable polymer. Examples of suitable such materials include synthetic polymers selected from poly(amides), poly(esters), poly(ester amides), poly(anhydrides), poly(orthoesters), polyphosphazenes, pseudo poly(amino acids), poly(glycerol-sebacate) (PGS), copolymers thereof, and mixtures thereof. In a preferred embodiment, the resorbable synthetic polymers are selected from poly(lactic acids), poly(glycolic acids), poly (lactic-co-glycolic acids), poly(caprolactones), and mixtures thereof. Other curable bioresorbable elastomers include poly (caprolactone) (PC) derivatives, amino alcohol-based poly (ester amides) (PEA) and poly (octane-diol citrate) (POC). PC-based polymers may require additional cross-linking agents such The tube of a drug reservoir portion tube may be substantially linear and in some cases may be substantially cylindrical with a circular cross-section, although square, triangle, hexagon, and other polygonal cross-sectional shapes can be used, among others.

The device body also may be configured to maintain the retention shape without, or at least without requiring, a retention frame. For example, the device body may include a "backbone" that holds the device in its retention shape. The "backbone" may be a thicker and/or stronger section of the material from which the drug reservoir portion is formed. The "backbone" may traverse the length of the drug reservoir portion, either linearly, spirally, or tortuously. In a particular embodiment, the device body is formed with a material that is treated or altered so that the device is deformable between a retention shape and a deployment shape. For example, the material used to form the drug reservoir portion may "memorize" and spontaneously assume the relatively expanded shape upon the application of heat to the device, such as when exposed to body temperatures upon entering the bladder. In some instances, the heating may cause at least a portion of the polymeric material to cross-link so that the device is capable of retaining the retention shape upon deployment in the bladder.

The ends of the tube may be sealed to limit escape of the drug, such as with a sealing structure or other sealing means. The sealing structure may have any shape suited to plug or close the tube end, such as a cylinder 120 as shown in FIG. 1, a ball 416 as shown in FIG. 4, a disk or a cylinder 808 as shown in FIG. 8A. In some embodiments, the sealing structure may have a larger diameter than the inner diameter of the tube, such that the tube stretches to fit snugly about the sealing structure, closing the tube and retaining the sealing structure in place. An example is shown in FIG. 8A. The sealing structure may be formed from biocompatible material, including a metal such as stainless steel, a polymer such as silicone, a ceramic, sapphire, or adhesive, among others or combinations thereof. The material may be biodegradable or bioerodible. A medical grade silicone adhesive or other adhesive also may be loaded into the tube in a workable form and may then cure within the tube to seal the end.

In some embodiments, the tube may have multiple reservoirs. Each reservoir may be defined by a portion of the tube inner surface and at least one partition. The partition may be a partition structure or plug inserted into the tube, such as a cylinder, sphere, or disk, among others, in which case the partition structure may have a larger cross-section than the tube, securing the partition structure in place and segregating adjacent reservoirs. For example, the cylindrical plug 808 of FIG. 8A that closes the tube end may instead serve as a partition structure to segregate two reservoirs positioned adjacent to each other along the length of the tube. The partition may be non-porous or semi-porous, non-resorbable or resorbable and may be formed of a material described above with reference to the cylindrical plug 808. The partition also may be formed in the tube, such as by molding. For example, one or more webs may extend through the tube along its length to segregate axial reservoirs that extend along the length of the tube, as shown in Examples J through L of FIG. 10. The partition also may be a structure that joins two different tubes that serve as separate reservoirs, as shown in Examples M through O of FIG. 10.

The multiple reservoirs permit segregating two or more different drug formulations in different reservoirs, delivering a single drug from different reservoirs at different rates or times following implantation, or combinations thereof. For example, two different reservoirs may have different configurations, such as different materials, different permeabilities, different numbers or placements of apertures (or the absence of apertures), different timing membranes in the apertures, among others or combinations thereof. The two different reservoirs also may house the same or different drug formulations in the same or different forms (such as liquid, semi-solid, and solid), or combinations thereof. The two different reservoirs further may be configured to release drug via different release mechanisms, such as via osmosis through an aperture and by diffusion through a drug reservoir wall that may lack an aperture completely. Coatings or sheaths also may be provided along different portions of a single drug reservoir or along different drug reservoirs housing the same or different drug formulations. These embodiments can be combined and varied to achieve the desired release profile of the desired drug.

In one embodiment, the total volume of the reservoir (or combined reservoirs) is sufficient to contain all the drug needed for local delivery over the course of a single treatment, reducing the number of procedures needed to treat a particular condition.

Apertures

In some embodiments, the device includes one or more apertures or orifices for dispensing the drug, such as via osmosis, diffusion, or a combination thereof, among other. The apertures may be spaced along the tube to provide a passageway for release of the drug formulation. The apertures or orifices may be positioned through a sidewall or an end of the tube. The apertures may be in fluid communication with one or more reservoirs. Embodiments of apertures are shown on the drug reservoir portions in FIGS. 1, 3, and 8 as apertures 118, 318, and 810, respectively.

The aperture may be located about a middle of the drug reservoir portion or adjacent to its exit, which may affect the ease of loading solid drug units into the drug reservoir portion as described below. The apertures may be positioned away from a portion of the tube that will be folded during insertion to limit tearing of degradable membranes on the apertures.

The aperture may be positioned inside the perimeter of the device, outside of the perimeter of the device, or an upper or lower plane of the device. For example, as shown in FIG. 3, the aperture 118 may be formed through the wall 122 of the drug reservoir lumen 108 on an opposite side from the wall 124 of the retention frame lumen 110. For example, the device 100 includes an aperture 118 located on an outside perimeter of the device, but in other embodiments the aperture is located on an upper plane of the device. An aperture positioned on the inside perimeter or on the upper or lower plane of the device advantageously may be less likely to become positioned directly adjacent to a portion of the implantation site, such as the bladder wall, delivering a large quantity of drug to one particular location. The aperture also may be formed in a groove or indent defined between the walls of the drug reservoir portion and the retention frame portions, so that the walls serve as bumpers that impede the aperture from becoming positioned directly adjacent to the implantation site. For example, the orifice 118 may be formed in a groove or indent defined between the walls 122, 124 of the drug reservoir lumen 108 and the retention frame lumen 110.

For ease of manufacturing, the aperture may be formed through the wall of the drug reservoir portion on an opposite side from the retention frame portion, as shown in FIG. 3. When the aperture is positioned opposite from the retention frame portion, it may be desirable to secure the retention frame portion below the device as described above, so that the aperture becomes positioned above the device, reducing the risk of the aperture becoming positioned on the outside perimeter of the device. However, other configurations are possible.

The size, number, and placement of the apertures may be selected to provide a controlled rate of release of the drug. A device that operates primarily as an osmotic pump may have one or more apertures sized small enough to reduce diffusion of the drug through the aperture(s), yet large enough and spaced appropriately along the tube to reduce the buildup of hydrostatic pressure in the tube. Within these constraints, the size and number of apertures for a single device (or reservoir) can be varied to achieve a selected release rate. In exemplary embodiments, the diameter of the aperture is between about 20 μm and about 800 μm, such as between about 25 μm and about 500 μm, and more particularly between about 30 μm and about 400 μm. In one example, the aperture has a diameter between about 100 μm and about 300 μm, such as about 150 μm. In embodiments where the device operates primarily by diffusion, the apertures may be in this range or larger. A single device may have apertures of two or more different sizes. The aperture may be circular, although other shapes are possible and envisioned, with the shape typically depending on manufacturing considerations. Examples of processes for forming the apertures include mechanical punching, laser drilling, laser ablation, and molding. The aperture may slightly taper from an exterior to an interior of the tube, and the aperture may be created either before or after the drug is loaded into the tube. The aperture also may be formed in an orifice structure disposed in an end of the tube, such as a ruby or sapphire precision orifice structure known in the art.

In some embodiments, the drug reservoir portion may not have any apertures, in which case the drug may be released via a release mechanism other than osmosis, such as diffusion through the wall of the drug reservoir portion. Similarly, a drug reservoir portion having multiple discrete drug reservoirs may have apertures associated with all, some, or none of the drug reservoirs, in which cases release from the different drug reservoirs may occur via different release mechanisms.

Degradable Membranes

In one embodiment, a degradable membrane, i.e., a timing membrane, is disposed over or in the apertures (e.g., in register with the aperture) to control the onset of release of the drug formulation. The degradable membrane may be a coating over all or some of the outer surface of the tube or a discrete membrane above or within the aperture. Two or more degradable membranes also may be used to control release from one aperture. The membranes may be formed, for example, of a resorbable synthetic polymer (such as polyester, a poly(anhydride), or a polycaprolactone) or a resorbable biological material (such as cholesterol, other lipids and fats). An example degradable membrane 812 is shown in FIG. 8B, and additional details are described in U.S. Patent Application Publication No. 2009/0149833.

The Drug Formulation and Solid Drug Tablets

The drug formulation can include essentially any therapeutic, prophylactic, or diagnostic agent, such as one that would be useful to deliver locally to a body cavity or lumen or regionally about the body cavity or lumen. The drug formulation may consist only of the drug, or one or more pharmaceutically acceptable excipients may be included. The drug may be a biologic. The drug may be a metabolite. As used herein, the term "drug" with reference to any specific drug described herein includes its alternative forms, such as salt forms, free acid forms, free base forms, and hydrates. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

In a preferred embodiment, the drug formulation is in a solid or semi-solid form in order to reduce the overall volume of the drug formulation and thereby reduce the size of the device, facilitating implantation. The semi-solid form may be, for example, an emulsion or suspension; a gel or a paste. In many embodiments, the drug formulation desirably includes no or a minimum quantity of excipient for the same reasons of volume/size minimization.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base. High solubility drugs may be suited for release due to an osmotic pressure gradient, such as via one or more apertures or passing pores through the device wall, while low solubility drugs may be suited for release via diffusion, such as directly through the device wall or through one or more apertures or passing pores in the device wall. For example, lidocaine base may be released via diffusion through a silicone wall without an aperture, and the release rate may be increased by adding apertures to the wall. Thus, the drug may be formulated to have a high or low solubility depending on the intended release mode. In one embodiment, the drug is formulated to improve its apparent solubility in the implantation environment, such as its apparent solubility in urine within the bladder.

In one embodiment, the devices provide pain relief to the patient. A variety of anesthetic agents, analgesic agents, and combinations thereof may be used. In embodiments, the device delivers one or more local anesthetic agents. The local anesthetic agent may be a cocaine analogue. In particular embodiments, the local anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These local anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones.

Other examples of drugs that may be used in the treatment of IC include nerve growth factor monoclonal antibody (MAB) antagonists, such as Tanezumab, and calcium channel alpha-2-delta modulators, such as PD-299685 or gabapentin.

Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-a2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

The drug delivery device is used in association with the placement of a ureteral stent, such as to treat pain, urinary urgency or urinary frequency resulting from ureteral stent placement. Non-limiting examples of specific drugs for such treatment include antimuscarinics, α-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, antimuscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In another embodiment, the drug delivery device is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an antileukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lows Therapeutics), urocanic acid, OGX 427 (OncoGenex), and SCH 721015 (Schering-Plough). The drug treatment may be coupled with a conventional radiation or surgical therapy targeted to the cancerous tissue.

In still another embodiment, the present intravesical drug delivery device is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the present drug delivery device is used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

The implantable drug delivery device also may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal cord* 42:267-72 (2004).

In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

The excipient of the drug formulation may be a matrix material, selected to modulate or control the rate of release of the drug from the reservoir. In one embodiment, the matrix material may be a resorbable or non-resorbable polymer. In another embodiment, the excipient comprises a hydrophobic or amphiphilic compound, such as a lipid (e.g., a fatty acids and derivatives, mono-, di- and triglycerides, phospholipids, sphingolipids, cholesterol and steroid derivatives, oils, vitamins and terpenes). The drug formulation may provide a temporally modulated release profile or a more continuous or consistent release profile. Other drugs and excipients may be used for other therapies.

Figure 6:
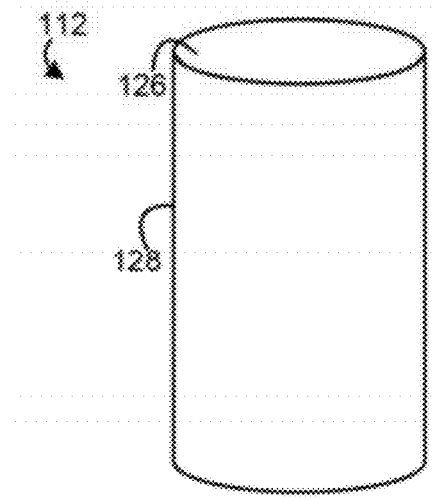
FIG. 6 is a perspective view of an embodiment of a solid drug tablet for use in some embodiments of the drug delivery devices described herein.

In a preferred embodiment, the drug formulation is in solid form. For example, the drug formulation is formed into solid drug units that are loaded into the drug reservoir portion. Each of the drug units is a solid, discrete object that substantially retains a selectively imparted shape (at the temperature and pressure conditions to which the delivery device normally will be exposed during assembly, storage, and handling before implantation). The drug units may be in the form of tablets, pellets, or beads, although other configurations are possible. For example, FIG. 6 illustrates a solid drug tablet 112 for implantation, and FIGS. 1-2 illustrate a number of the solid drug units 112 loaded into the drug reservoir lumen 108 of the drug delivery device 100.

The drug tablets made by a direct compression tableting process, a molding process, or other processes known in the pharmaceutical arts. The tablets optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in vivo dissolution and drug release characteristics. The drug formulation also may be loaded into the drug reservoir in workable form and may cure therein. Thereafter, the solidified drug may be broken along the length of the drug reservoir to form the interstices or breaks that permit device deformation. For example, in embodiments in which the drug formulation is configured to be melted and solidified, the drug formulation can be melted, injected into the drug reservoir in melted form, solidified in the drug reservoir, and broken into pieces in the drug reservoir to accommodate device deformation or movement. The drug formulation also may be extruded with the drug reservoir, may cure within the drug reservoir, and subsequently may be broken along the length of the reservoir to accommodate device deformation.

The drug tablet includes a drug content and may include an excipient content. The drug content includes one or more drugs or active pharmaceutical ingredients (API), while the excipient content includes one or more excipients. The term "excipient" is known in the art, and representative examples of excipients useful in the present drug tablets may include ingredients such as binders, lubricants, glidants, disintegrants, colors, fillers or diluents, coatings and preservatives, as well as other ingredients to facilitate manufacturing, storing, or administering the drug tablet.

In order to maximize the amount of drug that can be stored in and released from a given drug delivery device of a selected (small) size, the drug tablet preferably comprises a high weight fraction of drug or API, with a reduced or low weight fraction of excipients as are required for tablet manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a drug tablet that has 90% by weight of a drug in salt form may include less than 90% by weight of that drug in free base form.

In one embodiment, the drug tablet is more than 50% by weight drug. In a preferred embodiment, 75% or more of the weight of the drug tablet is drug, with the remainder of the weight comprising excipients, such as lubricants and binders that facilitate making the drug tablet. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the drug tablet. In some cases, the drug content comprises about 75% or more of the weight of the drug tablet. More particularly, the drug content may comprise about 80% or more of the weight of the drug tablet. For example, the drug content may comprise between about 85% and about 99.9% of the weight of the drug tablet. In some embodiments, the excipient content can be omitted completely.

In one embodiment, the drug and excipients are selected and the tablet formulated to be water soluble, so that the drug tablets can be solubilized when the device is located within the vesical, to release the solubilized drug. In a preferred embodiment, the drug tablets are formulated to be sterilizable, either within or outside of the drug delivery device, without substantial or detrimental changes in the chemical or physical composition of the drug tablets. Such drug tablets may be quite different from conventional drug tablets, which typically include active ingredients that constitute less than 50% of the drug tablet content by weight, with the remainder of the drug tablet comprising excipients that are often insoluble and/or may not be suited for conventional sterilization. Furthermore, the present drug tablets may be sized and shaped for use with an implantable drug delivery device. For example, the drug tablets may be "mini-tablets" that are much smaller in size than conventional tablets, which may permit inserting the drug tablets through a lumen such as the urethra into a cavity such as the bladder.

In embodiments in which one or more pharmaceutically acceptable excipients are included, the excipients may facilitate loading the solid drug units in the device. For example, the excipients may increase the lubricity of the drug units so that the drug units can slide with reference to the interior lumen walls of the drug reservoir portion. The excipients also may facilitate forming the therapeutic agent or agents into a solid drug tablet that can be loaded into the drug reservoir portion. The excipients also may affect the kinetics of drug release from the device, such as by increasing or retarding the solubility or dissolution rate of the drug units. In some embodiments, however, the drug release rate is predominately controlled by characteristics of the drug reservoir, such as the tube thickness and permeability to water or urine, while the excipient content of the drug units is primarily selected to permit reliable production of drug units that are solid and include a relatively high weight fraction of drug.

The individual drug units may have essentially any selected shape and dimension that fits within the device. In one embodiment, the drug units are sized and shaped such that the drug reservoir portion is substantially filled by a select number of drug units. Each drug unit may have a cross-sectional shape that substantially corresponds to a cross-sectional shape of the drug reservoir portion. For example, the drug units 112 are substantially cylindrical in shape as shown in FIG. 6 for positioning in the substantially cylindrical drug reservoir lumen 108 shown in FIG. 3. Once loaded, as shown in FIG. 3, the drug units 112 substantially fill the drug reservoir lumen 108, forming the drug reservoir portion 102.

The drug units may have outer dimensions that are about the same as, are slightly less than, or slightly exceed inner dimensions of the drug reservoir portion.

In embodiments, the drug units are shaped to align in a row when housed in the drug reservoir. Each drug unit has a cross-sectional shape that corresponds to the cross-sectional shape of the drug reservoir, and each drug unit may have end face shapes that correspond to the end faces of adjacent drug units. Thus, once the drug tablets are loaded in the drug reservoir, the line or row of drug tablets may substantially fill the drug reservoir with interstices or breaks formed between adjacent drug units. The interstices or breaks accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

An example is shown in FIG. 6, which illustrates the drug unit 112 having circular flat end faces 126 and a cylindrical side wall 128. Thus, the drug unit 112 can be aligned in a row with other drug units 112 for loading into the cylindrical drug reservoir lumen 108 as shown in FIG. 3. As shown in FIGS. 1-2, when so loaded, the drug units 112 substantially fill the drug reservoir lumen 108, with interstices or breaks 116 formed between them to accommodate deformation or movement. The flat end faces 126 permit piecewise flexibility of the device while limiting the volume or space within the drug reservoir portion that is devoted to the interstices or breaks 116. Thus, the device can be substantially filled with solid drug while retaining its flexibility. The tablet uniformity advantageously enables reproducibility in producing the medical product and thereby generally provides reliable, repeatable drug release characteristics.

In some embodiments, each drug unit may have a length that exceeds its width, meaning an aspect ratio of height:width that is greater than 1:1. Suitable aspect ratios for the drug units may be in the range of about 3:2 to about 5:2, although other aspect ratios are possible, including aspect ratios that are less than 1:1, like conventional drug tablets. An example is shown in FIG. 6, which illustrates the drug unit 112 with a length that exceeds its diameter.

In embodiments in which the solid drug tablets are designed for insertion or implantation in a lumen or cavity in the body, such as the bladder, via a drug delivery device, such as a device of the type described above with reference to FIG. 1, the drug tablets may be "mini-tablets" that are suitably sized and shaped for insertion through a natural lumen of the body, such as the urethra. For the purpose of this disclosure, the term "mini-tablet" generally indicates a solid drug tablet that is substantially cylindrical in shape, having end faces that are relatively planar or flat and a side face that is substantially cylindrical. An example mini-tablet is shown in FIG. 6. The mini-tablet 112 has a diameter, extending along the end face 126, in the range of about 1.0 to about 3.2 mm, such as between about 1.5 and about 3.1 mm. The mini-tablet 112 has a length, extending along the side face 128, in the range of about 1.7 mm to about 4.8 mm, such as between about 2.0 mm and about 4.5 mm. The friability of the tablet may be less than about 2%. Embodiments of solid drug tablets and systems and methods of making the same are further described below with reference to U.S. Patent Application Publication No. 2010/0330149 A1 to Daniel et al., which is incorporated by reference herein.

In a preferred embodiment, the drug tablets include lidocaine. A drug delivery device having drug tablets that primarily comprise lidocaine may be wholly deployed in the bladder of a patient in need of treatment for interstitial cystitis, neurogenic bladder, or pain, among others. Other diseases or conditions may also be treated using this device. In other embodiments, other drugs, alone or in combination with lidocaine, may be used to treat interstitial cystitis or other diseases and conditions involving the bladder.

Once the solid drug tablets are formed, the drug tablets may be loaded into the drug delivery device. After the device is loaded, the device preferably is sterilized. The selected sterilization process does not undesirably alter the physical or chemical composition of the solid drug tablets or other components of the device. Examples of suitable sterilization processes include gamma irradiation or ethylene oxide sterilization, although other sterilization processes may be used. For example, gamma irradiation at a strength of about 8 KGy to about 40 KGy, such as about 25 KGy, can be employed.

In addition, the drug tablets can be sterilized before or after loading/assembly into a drug delivery device, and the drug tablets possess a commercially reasonable shelf life. Once implanted, the composition of the drug tablets is appropriate for the intended route of administration, is stable in acidic conditions, and provides pre-selected, reproducible drug release kinetics. For example, the drug tablets may be solubilized in the bladder to continuously release drug at a suitably stable rate drug over an extended period.

Although mini-tablets and other solid drug tablets are described above as having a high weight fraction of drug or API and a low weight fraction of excipients, the solid drug tablets may have any weight fraction of drug, especially in cases in which the tablet includes a drug that is extremely potent, a stabilizing agent, or an agent that increases the solubility of the drug, among others or combinations thereof.

The Retention Frame Portion

The drug delivery device may include a retention frame portion. The retention frame portion is associated with the drug reservoir portion and permits retaining the drug reservoir portion in the body, such as in the bladder. The retention frame portion may include a retention frame that is deformable between a relatively expanded shape and a relatively lower-profile shape. That is, the retention frame may have a certain elastic limit and modulus that allows the device to be introduced into the body in a relatively lower-profile shape but then permits the device to return the relatively expanded shape once inside the body. The device may also have a sufficient elastic modulus to impede the device from assuming the relatively lower-profile shape once implanted, so as to limit or prevent accidentally expulsion of the device from the body under expected forces.

For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape may be shaped for retention in a body cavity, and the retention frame in the relatively lower-profile shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted. Such a configuration may limit or prevent accidental expulsion of the device from the body under expected forces. For example, the device may be retained in the bladder during urination or contraction of the detrusor muscle.

In one embodiment, the retention frame includes or consists of an elastic wire. In one embodiment, the elastic wire may comprise a biocompatible shape-memory material or a biodegradable shape memory polymer as described in U.S. Pat. No. 6,160,084 to Langer et al. The elastic wire also may include a relatively low modulus elastomer, which may be relatively less likely to irritate or cause ulcer within the bladder or other implantation site and may be biodegradable so that the device need not be removed. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

For example, in the embodiment shown in FIGS. 1-2, the retention frame 114 is an elastic wire formed from a superelastic alloy, such as nitinol, and surrounded by the wall 124 of the retention frame lumen 110, which forms a protective sheath about the retention frame 114. Thus, the wall 124 may be formed from a polymer material, such as silicone. In other embodiments, the retention frame may be an elastic wire formed from a superelastic alloy, such as nitinol, that is covered in a polymer coating, such as a silicone sheath and is attached to the drug reservoir portion.

In some embodiments, the retention frame lumen 110 may include the retention frame 114 and a filling material, such as a polymer filling. An example filling material is a silicone adhesive, such as MED3-4213 by Nusil Technology LLC, although other filling materials may be used. The filling material may fill the void in the retention frame lumen 110 about the retention frame 114. For example, the filling material may be poured into the retention frame lumen 110 about the retention frame 114 and may cure therein. The filling material may reduce the tendency of the drug reservoir lumen 108 to stretch along, or twist or rotate about, the retention frame 114, while maintaining the drug reservoir lumen 108 in a selected orientation with reference to the retention frame 114. The filling material is not necessary, however, and may be omitted.

When the retention frame is in the relatively expanded shape, such as the coiled shapes shown in FIGS. 1 and 4, the device may occupy a space having dimensions suited to impede expulsion from the bladder. When the retention frame is in the relatively lower-profile shape, such as the elongated shapes shown in FIGS. 2 and 5, the device may occupy an area suited for insertion into the body, such as through the working channel of a deployment instrument. The properties of the elastic wire cause the device to function as a spring, deforming in response to a compressive load but spontaneously returning to its initial shape once the load is removed. The polymer coating may make the outer surface of the retention frame relatively smooth and soft, reducing irritation of the bladder.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame comprises a shape-memory material, the material used to form the frame may "memorize" and spontaneously assume the relatively expanded shape upon the application of heat to the device, such as when exposed to body temperatures upon entering the bladder.

The retention frame may be in a form having a high enough spring constant to retain the device within a body cavity, such as the bladder. A high modulus material may be used, or a low modulus material. Especially when a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or sub-circles. The ends of the elastic wire may be adapted to avoid tissue irritation and scarring, such as by being soft, blunt, inwardly directed, joined together, or a combination thereof.

Figure 9:
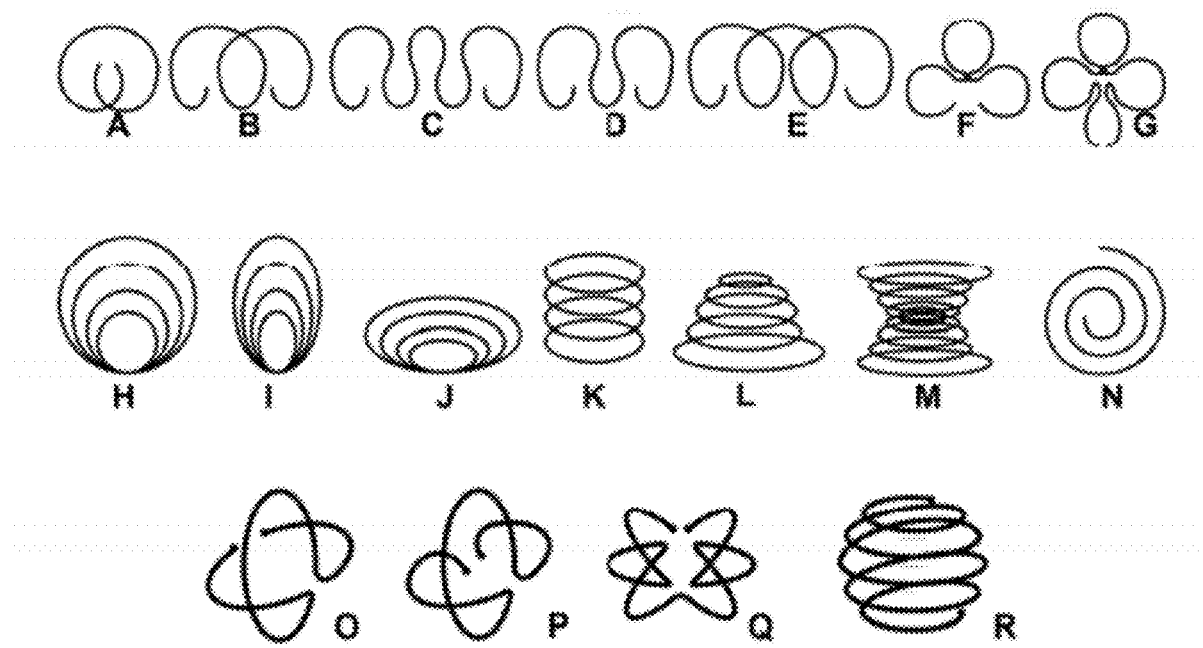
FIG. 9 illustrates examples of shapes for a retention frame of a drug delivery device.

Examples are shown in FIG. 9. The retention frame may have a two-dimensional structure that is confined to a plane, a three-dimensional structure, such as a structure that occupies the interior of a spheroid, or some combination thereof. In particular, Examples A through G illustrate frames comprising one or more loops, curls, or sub-circles, connected either linearly or radially, turning in the same or in alternating directions, and overlapping or not overlapping. Examples H through N illustrate frames comprising one or more circles or ovals arranged in a two-dimensional or a three-dimensional configuration, the circles or ovals either closed or opened, having the same or different sizes, overlapping or not overlapping, and joined together at one or more connecting points. The retention frame portion also may be a three-dimensional structure that is shaped to occupy or wind about a spheroid-shaped space, such as a spherical space, a space having a prorate spheroid shape, or a space having an oblate spheroid shape. Examples O through R illustrate retention frame portions that are shaped to occupy or wind about a spherical space, with each retention frame portion shown above a representation of the frame in a sphere. The retention frame portion may generally take the shape of two intersecting circles lying in different planes as shown in Example O, two intersecting circles lying in different planes with inwardly curled ends as shown in Example P, three intersecting circles lying in different planes as shown in Example Q, or a spherical spiral as shown in Example R. In each of these examples, the retention frame portion can be stretched to the linear shape for deployment through a deployment instrument. The retention frame portion may wind about or through the spherical space, or other spheroid-shaped space, in a variety of other manners. One or both of the retention frame and retention housing may be omitted, in which case the retention portion may be components of the drug portion itself, which may assume or may be deformed into a retention shape, or the retention portion may be an anchor associated with the drug portion.

Other Device Features

The drug reservoir portion can include a coating or a sheath, which may be substantially impermeable to water or relatively less permeable to water than the drug reservoir portion to reduce or alter the osmotic or diffusive surface area of the device body. Thus, the release rate can be independently controlled or targeted with reduced adjustment of desired device characteristics, such as size, shape, material, permeability, volume, drug payload, flexibility, and spring constant, among others. To achieve the release rate, the coating or sheath may cover all or any portion of the device body, and the coating or sheath may be relatively uniform or may vary in thickness, size, shape, position, location, orientation, and materials, among others and combinations thereof. Further, multiple coatings or sheaths may be provided along different portions of the device body, about the same drug reservoir or different drug reservoirs housing the same or different drug formulations. In cases in which the drug reservoir portion is formed from silicone tubing, for example, a coating may be formed from parylene, while a sheath may be formed from a polymer such as polyurethane or curable silicone, or another biocompatible coating or sheath material known in the art. In some embodiments, the coating or sheath may be positioned on the tube between the end and the orifice so that water permeating through the tube adjacent to the end can drive through the portion of the tube covered by the sheath and out of the orifice, reducing or avoiding isolation or stagnation of the drug under the sheath. Examples of sheaths are 814 illustrated in FIG. 8A. Coatings and sheaths, and equations for selecting such designs, are described in U.S. Patent Publication No. 2009/0149833.

Figure 5:
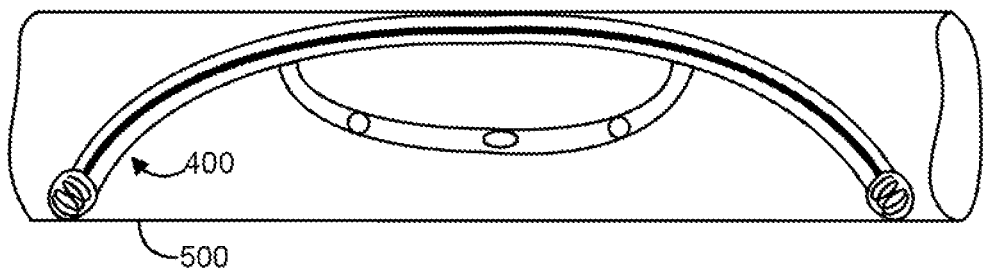
FIG. 5 is a plan view of the drug delivery device shown in FIG. 4, illustrating the drug delivery device inside a deployment instrument.

In one embodiment, the device includes at least one radio-opaque portion or structure to facilitate detection or viewing (e.g., by X-ray imaging or fluoroscopy) of the device by a medical practitioner as part of the implantation or retrieval procedure. In one embodiment, the tube is constructed of a material that includes a radio-opaque filler material, such as barium sulfate or another radio-opaque material known in the art. Some tubing may be made radio-opaque by blending radio-opaque fillers, such as barium sulfate or another suitable material, during the processing of the tubing. The radio-opaque material also may be associated with the retention frame. For example, as shown in FIGS. 4-5, a platinum wire 410 may be wound about ends of the elastic wire 406 and covered in smoothening material 412. Ultrasound imaging may be used. Fluoroscopy may be the preferred method during deployment/retrieval of the non-erodible device by providing accurate real-time imaging of the position and orientation of the device to the practitioner performing the procedure.

In one embodiment, the body of the implantable drug delivery device further includes at least one retrieval feature, such as a structure that facilitates removal of the device from the body cavity, for example for removal of a non-resorbable device body following release of the drug formulation.

One example of a retrieval feature is a string, formed of a biocompatible material. The string may be attached to a mid-portion or an end-portion of the drug delivery device. In some embodiments, the string is sized to extend along the urethra from the bladder to the exterior of the body, in which case a proximal end of the string may be positioned outside of the body once the device is positioned in the bladder. The string also may be shorter in size, so that once the device is positioned in the bladder, the proximal end of the string is positioned in the urethra in a location that is reachable by a physician. In either case, the device may be removed from the bladder by engaging the string to pull the device through the urethra. In such embodiments, the diameter of the string may be sized to fit comfortably in the urethra during the period of implantation. In other embodiments, the string is sized to be wholly implanted in the bladder with the device, in which case the string facilitates locating and grasping the device within the bladder using a removal instrument positioned in the urethra, such as a cystoscope or catheter.

In embodiments in which the string is attached to a mid-portion of the drug delivery device, the device may fold upon itself as it enters the removal instrument or the urethra. Folding at the mid-portion may be facilitated once the drug delivery device has released at least a portion of the drug or is empty. In embodiments in which the string is attached to an end-portion of the drug delivery device, the device may move into the deployment shape as it enters the removal instrument or the urethra. Thus, the deployment shape also may be considered a retrieval shape in such embodiments.

Embodiments of retrieval features also are described in U.S. Patent Publication No. 2007/0202151 A1. In these and in other embodiments, the device may be retrieved using conventional endoscopic grasping instruments.

Combination of the Components

The drug reservoir portion and the retention frame portion are associated with each other to form the drug delivery device. A variety of different associations are envisioned. For example, the drug reservoir portion and the retention frame portion may be at least partially aligned. In other words, the drug reservoir portion may extend along a portion or the entire length of the retention frame portion, substantially parallel or coincident with the retention frame portion. An example of such an embodiment is shown in FIGS. 1-3.

In other embodiments, the drug reservoir portion may be attached to only portion of the retention frame. The drug reservoir portion may have first and second end portions that are attached to an portion of the retention frame. The end portions of the drug reservoir may terminate at the retention frame, the end portions may overlap the retention frame, or a combination thereof. The drug reservoir portion may be oriented with reference to the retention frame portion such that the drug reservoir portion lies within the perimeter of the retention frame portion, beyond the perimeter of the retention frame portion, or a combination thereof. Additionally, a number of drug reservoir portions may be associated with a single retention frame portion. Examples A through E of FIG. 10 illustrate such embodiments.

Figure 10:
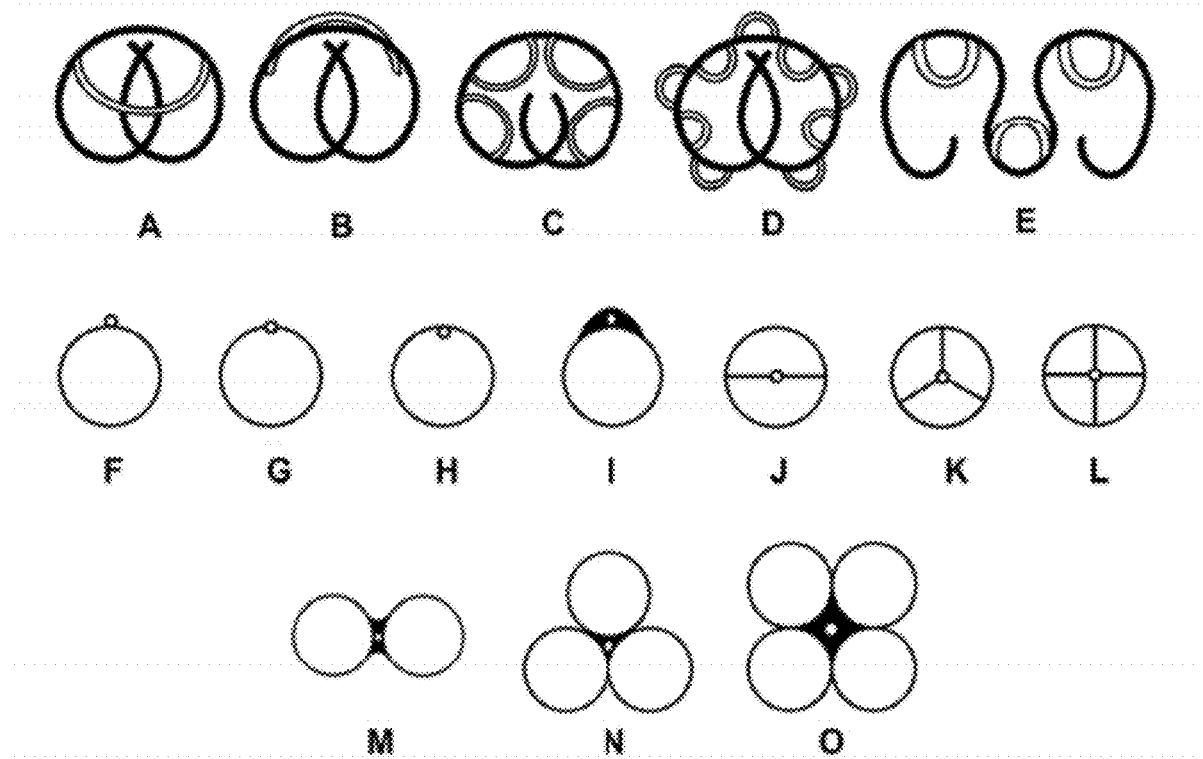
FIG. 10 illustrates examples of configurations for drug delivery devices having at least one drug delivery portion and a retention frame portion.

FIG. 10 also illustrates several alternative embodiments in cross-section. As shown in Examples F, G, H, and I, the retention frame wire may extend along either an exterior surface of the drug reservoir wall, along an interior surface of the drug reservoir wall, through the drug reservoir wall, or within a reinforced area inside or outside of the wall. As shown in Examples J, K, and L, the elastic wire may also be positioned within the interior of the tube supported by a web, which may partition the tube into multiple compartments. The web may be perforated or otherwise non-continuous so that the compartments are in communication with each other, or the web may be relatively continuous such that the compartments are segregated from each other to form different reservoirs that may be suited for holding different drug formulations. The web may be formed from the same material as the tube, or from a material having a different permeability to water or urine, depending on the embodiment. As shown in Examples M, N, and O, the elastic wire may be associated with multiple tubes, extending along or between the tubes. The elastic wire may be embedded in a reinforcement area that joins together multiple discrete tubes. The tubes may hold the same or different drug formulations and also may be formed from the same or different materials of construction, such as materials that differ in permeability to urine or other aqueous or bodily fluids.

In other embodiments, the drug reservoir portion and the retention frame portion may be the same component in some embodiments. In such cases, the device may comprise a tube formed in a configuration having a sufficient spring constant to retain the device in the body, as described above. Also, the drug reservoir portion may be wrapped around the retention frame portion, one or any number of times.

Furthermore, when the device is in the retention shape, the retention frame portion may have any orientation with reference to the drug reservoir portion, lying either inside, outside, above, or below the drug reservoir portion or moving with reference to the drug reservoir portion as the device moves through the implantation site. For example, the device 100 includes a retention frame portion that lies inside the perimeter of the drug reservoir portion. In other embodiments, the device includes a retention frame portion that lies below the drug reservoir portion (such that the retention frame portion would not be visible in FIG. 1). A particular orientation between the two portions can be maintained by filling the retention frame portion with a filling material, such as a silicone adhesive, after the retention frame is loaded. The tilling material may cure or solidify to prevent movement of one portion with reference to the other. Other means of maintaining the orientation of the retention frame portion with reference to the drug reservoir portion also can be used.

In the embodiment shown in FIG. 1, for example, the drug delivery device 100 is suited for delivering a drug into the bladder. The drug reservoir lumen 108 may have an inner diameter of about 1.3 to about 3.3 mm, such as about 1.5 to about 3.1 mm, an outer diameter of about 1.7 to about 3.7 mm, such as about 1.9 to about 3.4 mm, and a length of about 12 to 21 cm, such as about 14 to 16 cm. The drug reservoir lumen 108 may hold about 10 to 100 cylindrical drug tablets, such mini-tablets. The mini-tablets may each having a diameter of about 1.0 to about 3.3 mm, such as about 1.5 to about 3.1 mm, and a length of about 1.5 to about 4.7 mm, such as about 2.0 to about 4.5 mm. Such mini-tablets may have a lidocaine payload of about 3.0 to about 40.0 mg. One particular example of a mini-tablet may have a diameter of about 1.52 mm, a length of about 2.0 to 2.2 mm, and a mass of about 4.0 to 4.5 mg lidocaine. Another particular example of a mini-tablet may have a diameter of about 2.16 mm, a length of about 2.9 to 3.2 mm, and a mass of about 11.7 to 13.1 mg lidocaine. Yet another particular example of a mini-tablet may have a diameter of about 2.64 mm, a length of about 3.5 to 3.9 mm, and a mass of about 21.3 to 23.7 mg lidocaine. Still another particular example of a mini-tablet may have a diameter of about 3.05 mm, a length of about 4.1 to 4.5 mm, and a mass of about 32.7 to 36.9 mg lidocaine. However, other diameters, lengths, and masses can be used.

Within these ranges, the device may be designed to deliver between about 150 mg and 1000 mg of lidocaine to the bladder, such as about 200 mg, about 400 mg, about 600 mg, or about 800 mg of lidocaine. For example, a smaller payload may be delivered from a smaller device or from a device loaded with fewer tablets, the remainder of the space in the device being loaded with a spacer, filling material, or buoyancy material.

The foregoing specific configurations are merely possibilities of the type of devices that may be created by a person skilled in the art upon reading the present disclosure. For example, in some embodiments the drug reservoir portion may be omitted completely, and the retention frame portion may be associated with another component for retention in the body, such as the bladder. Examples of other components include diagnostic equipment, test materials, and small electronic devices, such as cameras and sensors, among others.

II. Method of Making the Device

An embodiment of a method of making an implantable drug delivery device may include forming a drug delivery device, forming a number of drug tablets, and loading the drug tablets into the drug delivery device. In embodiments, forming the drug delivery device may include one or more of the following sub-steps: forming a device body, forming a retention frame, associating the device body with the retention frame, and forming one or more apertures in the device body. In other embodiments, forming the drug delivery device may include one or more of the following sub-steps: forming a device body capable or maintaining a retention shape, and forming one or more apertures in the device body. In further embodiments, forming the drug delivery device may include one or more of the following sub-steps: forming a device body, treating the device body so that it will maintain a retention shape, and forming one or more apertures in the device body.

Forming the device body may include forming a flexible body having walls that define a drug reservoir lumen and, if necessary, a retention frame lumen. For example, the device body may be formed by extruding or molding a polymer, such as silicone. In particular, forming the device body may include integrally forming two tubes or walls that are substantially aligned and adjoined along a longitudinal edge. Alternatively, the two lumens may be separately formed and attached to each other, such as with an adhesive. Other methods of forming the device body also may be employed.

Forming a retention frame may include forming an elastic wire from, for example, a superelastic alloy or shape-memory material and "programming" the elastic wire to naturally assume a relatively expanded shape. Heat treatment may be used to program the elastic wire to assume the expanded shape. For example, the retention frame may be formed by forming the elastic wire into a pretzel shape and heat treating the elastic wire at a temperature over 500° C. for a period over five minutes. In embodiments in which the retention frame comprises a low modulus elastomer, the step of forming the vesical retention frame may comprising forming one or more windings, coils, loops or spirals in the frame so that the frame functions as a spring. For example, the retention frame may be formed by extrusion, liquid injection molding, transfer molding, or insert molding, among others. Similar techniques may be used to form a device body capable of assuming a retention shape without being associated with a retention frame.

Associating the device body with the retention frame may comprise inserting the retention frame into the retention frame lumen of the device body. In some embodiments, a distal end of the retention frame is blunted or is covered in a smooth ball of increased cross section during insertion of the retention frame into the lumen. The ball may facilitate driving the retention frame through the retention frame lumen without puncturing the wall of the device body. Also in some embodiments, the device body may be slightly compressed between two surfaces during the insertion of the retention frame. Compressing the device body elongates the opening into the retention frame lumen, facilitating loading.

In some embodiments, associating the device body with the retention frame further includes filling the retention frame lumen with a filling material after the retention frame is loaded. The filling material occupies the remainder of the lumen not occupied by the retention frame, reducing the ability of the device body to stretch along, or twist or rotate about, the retention frame. For example, silicone or another polymer may be injected or poured into the retention frame lumen and may cure therein. In other embodiments, associating the device body with the retention frame portion may comprise integrally forming the two portions together, such as by overmolding the device body about the retention frame.

Forming one or more apertures in the device body may include laser drilling or mechanically punching one or more holes in the device body.

The drug tablets made by a direct compression tableting process, a molding process, or other processes known in the pharmaceutical arts. The drug tablets may be loaded into the drug delivery device by any known method, including those described in U.S. Patent Application Publication No. 2010/0331770 A1 to Lee et al., which is incorporated herein by reference.

Some steps or sub-steps of the method of making an implantable drug delivery device may be performed in other orders or simultaneously. For example, the retention frame may be associated with the device body either before or after the drug units are loaded into the device body. Similarly, the apertures may be formed in the device body either before or after the drug tablets are loaded.

In embodiments, the method of making an implantable drug delivery device may further include partitioning the drug reservoir lumen into multiple discrete drug reservoirs, such as by positioning one or more partition structures within the drug reservoir lumen in an alternating fashion with the loading of the drug tablets. In embodiments, the method may further include sealing the drug tablets in the device body. The method may also include associating one or more release controlling structures with the drug reservoir lumen, such as a sheath or coating placed over at least a portion of the surface of the device body to control the rate of release of the drug or a degradable membrane positioned over or in one or more of the apertures to control the initial time of release of the drug therethrough.

In a preferred embodiment, the drug delivery device is sterilized, such as after the device is manufactured/assembled and before the device is implanted. In some cases, the device may be sterilized after the device is packaged, such as by subjecting the package to gamma irradiation or ethylene oxide gas.

III. Use and Applications of the Device

The device may be implanted in the bladder or other body cavity or lumen of a patient in need thereof. Subsequently, the device may release one or more drugs for the treatment of one or more conditions, locally to one or more tissues at the deployment site and/or regionally to other tissues distal from the deployment site. The release may be controlled over an extended period. Thereafter, the device may be resorbed, excreted, or some combination thereof.

Figure 11:
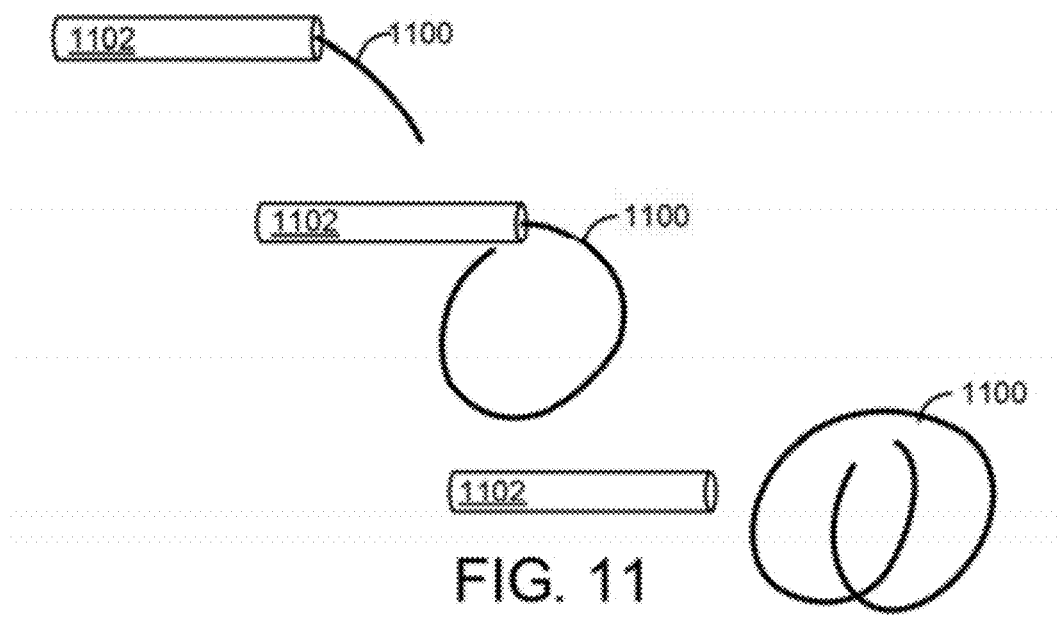
FIG. 11 illustrates a method of implanting a drug delivery device via a deployment instrument.

In one example, the device is implanted by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. An example is illustrated in FIG. 11, which shows the device 1100 assuming a retention shape as the device exits a deployment instrument 1102. The deployment instrument 1102 may be any suitable lumen device, such as a catheter, urethral catheter, or cystoscope. These terms are used interchangeably herein, unless otherwise expressly indicated.

The deployment instrument 1102 may be a commercially available device or a device specially adapted for the present drug delivery devices. Examples of suitable deployment instruments and techniques are described in U.S. Patent Application Publication No. 2011/0202036 to Boyko, et al., which is incorporated herein by reference.

Once implanted, the device may release the drug. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

Subsequently, the device may be retrieved from the body, such as in cases in which the device is non-resorbable or otherwise needs to be removed. Retrieval devices for this purpose are known in the art or can be specially produced. The device also may be completely or partially bioresorbable, such that retrieval is unnecessary, as either the entire device is resorbed or the device sufficiently degrades for expulsion from the bladder during urination. The device may not be retrieved or resorbed until some of the drug, or preferably most or all of the drug, has been released. If needed, a new drug-loaded device may subsequently be implanted, during the same procedure as the retrieval or at a later time.

Figure 12:
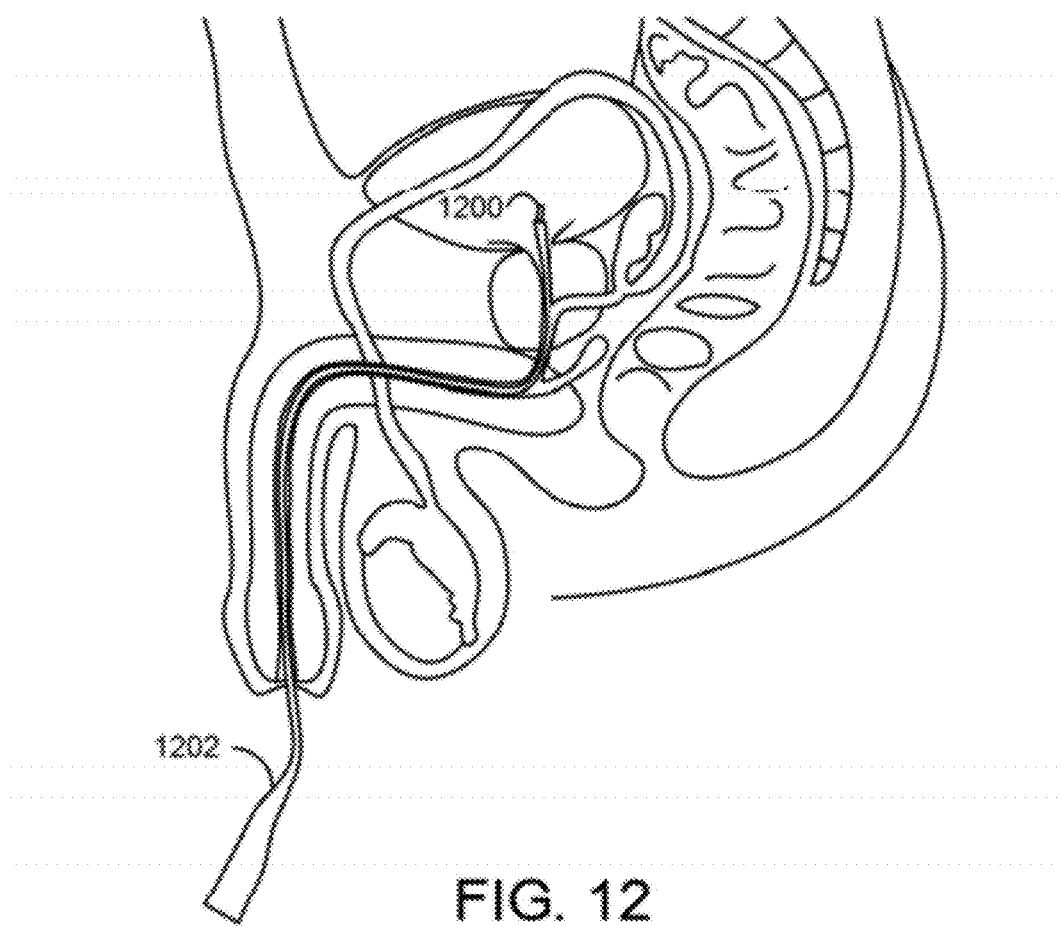
FIG. 12 is a sagittal view of a male patient, illustrating a drug delivery device exiting a deployment instrument into a bladder of the patient.

FIG. 12 illustrates the implantation of a device 1200 into the bladder, wherein the adult male anatomy is shown by way of example. A deployment instrument 1202 may be inserted through the urethra to the bladder, and the device 1200 may be passed through the deployment instrument 1202, driven by a stylet or flow of lubricant or other fluid, for example, until the device 1200 exits into the bladder. In this way, the device is implanted into the bladder of a male or female human patient in need of treatment, either adult or child.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one embodiment, the implantable device, with a self-contained drug payload, is deployed wholly within the bladder to provide local, sustained delivery of at least one drug locally to the bladder in an effective amount. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In some embodiments, the intravesical drug delivery device is deployed into the bladder of a patient for regional drug delivery to one or more nearby genitourinary sites. The device may release drug locally to the bladder and regionally to other sites near the bladder. Such delivery may provide an alternative to systemic administration, which may entail undesirable side effects or result in insufficient bioavailability of the drug.

In one embodiment, the intravesical drug delivery device is implanted into a bladder to locally deliver a local anesthetic agent for management of pain arising from any source, such as a disease or disorder in genitourinary tissues, or pain stemming from any bladder procedure, such as surgery, catheterization, ablation, medical device implantation, or stone or foreign object removal, among others. For example, a local anesthetic agent can be released into the bladder for regional delivery to nearby sites to manage nearby pain arising from any source, such as post-operative pain associated with the passage of a medical device into or through a ureter or other post-operative pain in sites apart from the bladder.

In one particular embodiment, a device having a payload of lidocaine may be delivered to the bladder, and lidocaine may be continuously released from the device over an extended period. Implanting lidocaine in solid form permits further reducing the size of the device to reduce bladder irritation and patient discomfort. In one embodiment, the device may have two payloads of lidocaine that are released at different times. The first payload may be adapted for relatively quick release, while the second payload may be adapted for more continuous release. For example, the first payload may be in liquid form or may be housed in a relatively fast-acting osmotic pump, such as a silicone tube having a relatively thinner wall, while the second payload may be solid form or may be housed in an osmotic pump that experiences an initial delay or induction time before releasing, such as a silicone tube having a relatively thicker wall. Thus, the method may continuously release lidocaine into the bladder during an initial, acute phase and during a maintenance phase. Such a method may compensate for an initial induction time of the device.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An implantable medical device for controlled drug delivery, comprising:
   a device structure which comprises a device body having at least one drug reservoir lumen, the device structure being deformable between a coiled retention shape and a low profile shape for deployment in the bladder of a patient;
   a drug formulation positioned in the at least one drug reservoir lumen, the drug formulation comprising at least one drug; and
   at least one buoyancy retention portion, which comprises at least one retention air element comprising a volume of entrapped air, the retention air element being wholly disposed within the at least one drug reservoir lumen and adjacent at least a portion of the drug formulation,
   wherein the buoyancy retention portion comprises a water permeable or biodegradable wall, which at least in part defines a space containing the volume of entrapped air,
   wherein the buoyancy retention portion is configured to release the entrapped air at a selected time following implantation of the device.

2. The device of claim 1, wherein the at least one retention air element is in the form of a hollow capsule or a closed-cell foam, the capsule or the cells of the foam containing the entrapped air.

3. The device of claim 1, wherein the drug formulation comprises a plurality of solid drug tablets disposed in the drug reservoir lumen.

4. The device of claim 1, wherein the drug comprises lidocaine.

5. The device of claim 1, wherein
   the buoyancy retention portion comprises the biodegradable wall, which degrades or erodes in vivo.

6. The device of claim 1, wherein
   the buoyancy retention portion comprises the water permeable wall, which is coated by a non-water-permeable coating that erodes or degrades in vivo.

7. The device of claim 1, wherein the at least one buoyancy retention portion is configured to release the entrapped air following release of at least a portion of the drug in vivo.

8. The device of claim 1, wherein the volume of entrapped air is sufficient to retain the device in the bladder during urination.

9. The device of claim 1, wherein the device body is a tube having a diameter of 5 mm or less in the coiled retention shape and in the low-profile shape.

10. An implantable medical device for controlled drug delivery, comprising:
- a device structure which comprises a device body having at least one drug reservoir lumen, the device structure being deformable between a coiled retention shape and a low-profile shape for deployment in the bladder of a patient;
- a drug formulation positioned in the drug reservoir lumen, the drug formulation comprising at least one drug; and
- at least one buoyancy retention portion, which comprises a gas-generating or effervescent powder disposed wholly within the at least one drug reservoir lumen, such that the gas-generating or effervescent powder and the drug formulation are disposed within a continuous volume of the drug reservoir lumen.

11. The device of claim 10, wherein the at least one buoyancy retention portion is expandable from a collapsed or compressed deployment form to an inflated form filled with gas produced from the gas-generating or effervescent powder.

12. The device of claim 10, wherein the at least one buoyancy retention portion comprises a water-permeable wall.

13. The device of claim 10, wherein the gas-generating or effervescent powder comprises:
- an organic acid or its acidic salt, and
- an alkali metal bicarbonate or carbonate.

14. The device of claim 10, wherein the gas-generating or effervescent powder comprises citric acid, malic acid, tartaric acid, adipic acid, fumaric acid, succinic acid, ascorbic acid, maleic acid, alginic acid, sodium dihydrogen phosphate, disodium hydrogen phosphate, or a combination thereof.

15. The device of claim 10, wherein the gas-generating or effervescent powder comprises sodium bicarbonate, potassium bicarbonate, calcium carbonate, sodium carbonate, potassium carbonate, or a combination thereof.

16. The device of claim 10, wherein the drug formulation comprises a plurality of solid drug tablets disposed in the drug reservoir lumen.

17. The device of claim 10, wherein the drug comprises lidocaine.

18. The device of claim 10, wherein the at least one buoyancy retention portion comprises a wall formed from a material that degrades or erodes in vivo.

19. The device of claim 10, wherein the at least one buoyancy retention portion comprises a wall formed of a water permeable material, which is coated by a non-water-permeable coating that erodes or degrades in vivo.

20. The device of claim 10, wherein the gas-generating or effervescent powder is configured to generate an entrapped gas sufficient to facilitate flotation of the device in the bladder upon deployment.

21. The device of claim 10, wherein the device body is a tube having a constant diameter in the coiled retention shape and in the low-profile shape.

22. The device of claim 21, wherein the diameter is 5 mm or less.

23. The device of claim 10, wherein the gas-generating or effervescent powder is configured to generate an entrapped gas and the at least one buoyancy retention portion is configured to release the entrapped gas following release of at least a portion of the drug in vivo.

24. The device of claim 10, wherein the gas-generating or effervescent powder is configured to generate an entrapped gas and the at least one buoyancy retention portion is configured to release the entrapped gas at a select time following implantation of the device.

25. The device of claim 10, wherein the gas-generating or effervescent powder is configured to generate an entrapped gas sufficient to retain the device in the bladder during urination.

26. An intravesical drug delivery device, comprising:
- an elongated device body having a first end, an opposed second end, and a drug reservoir lumen in the body between the first and second ends, the drug reservoir lumen having a first end and an opposed second end;
- a drug formulation positioned in the drug reservoir lumen; and
- at least one buoyancy retention element comprising a gas entrapped by a wall, wherein the wall entrapping the gas further defines the drug reservoir lumen and contains the drug formulation,
- wherein the device body is configured to be elastically deformable between a coiled retention shape and a low profile shape for deployment in the bladder of a patient,
- wherein the at least one buoyancy retention element is configured to release the entrapped gas at a select time following implantation of the device.

27. The device of claim 26, wherein the at least one buoyancy retention element comprises a hollow capsule or a closed-cell foam.

28. The device of claim 26, wherein the wall of the at least one buoyancy retention element comprises a water-permeable wall that is degradable or erodible in vivo.

29. The device of claim 26, wherein the apparent diameter of the device body is 5 mm or less.

30. The device of claim 26, wherein the entrapped gas is sufficient to facilitate flotation of the device in the bladder upon deployment.

31. The device of claim 26, wherein the at least one buoyancy retention element is configured to release the entrapped gas following release of at least a portion of the drug.

32. The device of claim 26, wherein the entrapped gas is sufficient to retain the device in the bladder during urination.

33. The device of claim 26, wherein the at least one buoyancy retention element is positioned between the first and second ends of the drug reservoir lumen.

* * * * *